United States Patent
Takeuchi et al.

(10) Patent No.: US 7,341,697 B2
(45) Date of Patent: Mar. 11, 2008

(54) REACTION CELL AND OPERATION METHOD THEREOF

(75) Inventors: Yukihisa Takeuchi, Aichi-pref (JP); Yasuko Yoshida, Nagoya (JP); Toshikazu Hirota, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 635 days.

(21) Appl. No.: 10/377,579

(22) Filed: Feb. 28, 2003

(65) Prior Publication Data
US 2004/0005722 A1 Jan. 8, 2004

(30) Foreign Application Priority Data
Mar. 1, 2002 (JP) ............... 2002-056041

(51) Int. Cl.
*B01L 3/00* (2006.01)
*G01N 29/00* (2006.01)

(52) U.S. Cl. ............... 422/102; 422/58; 422/99; 73/1.82

(58) Field of Classification Search ............ 422/99, 422/55, 68.1, 67, 102; 435/286.7; 204/221, 204/192.18; 416/79; 436/518; 366/187, 366/152.3, 154.2, 152.5
See application file for complete search history.

(56) References Cited

U.S. PATENT DOCUMENTS

| | | | |
|---|---|---|---|
| 2,742,408 A | | 4/1956 | LaPorte |
| 3,575,383 A | * | 4/1971 | Coleman .................. 366/115 |
| 3,596,883 A | * | 8/1971 | Brech .................... 366/115 |
| 3,859,050 A | * | 1/1975 | Horn et al. .............. 435/288.5 |
| 4,227,817 A | | 10/1980 | Gerry |
| 4,325,910 A | * | 4/1982 | Jordan .................... 422/64 |
| 4,433,916 A | | 2/1984 | Hall |
| 4,526,168 A | * | 7/1985 | Hassler et al. ............ 601/4 |
| 4,612,291 A | * | 9/1986 | Dawes .................... 436/174 |
| 4,742,030 A | * | 5/1988 | Masaki et al. ............ 501/105 |
| 4,849,340 A | * | 7/1989 | Oberhardt ................ 435/13 |
| 4,849,769 A | * | 7/1989 | Dressler .................. 347/27 |
| 4,909,266 A | * | 3/1990 | Massa .................... 134/60 |
| 5,395,592 A | | 3/1995 | Bolleman et al. |
| 5,674,742 A | | 10/1997 | Northrup et al. |
| 5,736,100 A | * | 4/1998 | Miyake et al. ........... 422/64 |
| 5,777,860 A | * | 7/1998 | Halbert .................. 363/34 |
| 5,877,580 A | | 3/1999 | Swierkowski |
| 5,912,182 A | | 6/1999 | Coakley et al. |

(Continued)

FOREIGN PATENT DOCUMENTS

EP 950889 A1 * 10/1999

(Continued)

*Primary Examiner*—Jill Warden
*Assistant Examiner*—Neil Turk
(74) *Attorney, Agent, or Firm*—Burr & Brown

(57) ABSTRACT

A reaction cell is provided with a vessel-like cell main body and a circular piezoelectric/electrostrictive oscillator fixed to an outside of a bottom surface of the cell main body. The cell main body includes a circular bottom plate portion and a circumferential wall portion which rises from a circumferential edge of the bottom plate portion so as to thereby surround the bottom plate portion. The bottom plate portion and the circumferential wall portion are integrally formed from ceramics. A solution accommodation space is formed above the bottom plate portion and is partially enclosed by the circumferential wall portion. The piezoelectric/electrostrictive oscillator is concentrically adhered to the outside of the bottom surface of the cell main body.

6 Claims, 16 Drawing Sheets

U.S. PATENT DOCUMENTS

| | | | |
|---|---|---|---|
| 5,922,591 A * | 7/1999 | Anderson et al. | 435/287.2 |
| 6,214,294 B1 * | 4/2001 | Shibutani et al. | 422/99 |
| 6,365,378 B1 * | 4/2002 | Hirota et al. | 435/91.1 |
| 6,372,506 B1 * | 4/2002 | Norton | 436/63 |
| 2002/0025579 A1 | 2/2002 | Odakura et al. | |

FOREIGN PATENT DOCUMENTS

| | | |
|---|---|---|
| JP | 02-226044 | 9/1990 |
| JP | 3-151084 | 6/1991 |
| JP | 11-14525 | 1/1999 |
| JP | 2001-215232 | 8/2001 |
| WO | 94/04265 | 3/1994 |

* cited by examiner

REACTION CELL AND OPERATION METHOD THEREOF

BACKGROUND OF THE INVENTION

1. Field of the Invention

The present invention relates to a reaction cell and, more specifically, to a reaction cell in which a biochemical reaction, such as an enzyme reaction or nucleic acid hybridization, proceeds, and a method of using the reaction cell to carry out and observe chemical reactions.

2. Description of the Related Art

Conventionally, detecting a degree of a reaction or identifying a characteristic of a sample, the nature of which is unknown, is achieved by receiving the sample into a reaction cell and, after the passage of a prescribed reaction length of time, carrying out calorimetric analyses or the like.

Hybridization between complementary nucleic acid strands is an effective method for detecting and identifying genetic materials. The hybridization reaction is a chemical technique wherein two nucleic-acid strands having complementary bases, such as the strands forming molecules of DNA, are bonded to each other to thereby form a double-stranded material. For performing an analysis of hybridized nucleic acid strands, one of the nucleic acid strands is labeled with, for example, a fluorescent material or tag before hybridization with its complementary nucleic acid strand. After hybridization is complete, the amount of labeled material present in the double-stranded material is detected in order to thereby measure the hybridized amount of material in the sample. Namely, the hybridization method is used for the estimation of abase sequence of an unknown nucleic acid material by means of detecting whether it has hybridized with its complementary counterpart. Detection of whether an unknown target genetic material is present in a sample occurs when a known base sequence of one nucleic acid strand contacts a complementary base sequence from the sample, which results in the two complementary nucleic acid strands being hybridized. The hybridized nucleic acid strands are then detected and quantified.

There are cases with various kinds of enzyme reactions, not limited to the above-described nucleic acid hybridization, where merely putting a relevant solution into the reaction cell results in a failure for the reaction to proceed with a high efficiency. For this reason, it is considered as being effective to vibrate and agitate the solution within the reaction cell by using a vibrator or an ultrasonic oscillator.

SUMMARY OF THE INVENTION

A reaction measuring device, a DNA analyzer, etc. each of which is provided with the above-described reaction cell, are desired to be miniaturized for the convenience of using it at a medical scene or a laboratory or in the field, etc. In accordance with this, it has also been demanded that the reaction cell itself should be miniaturized and made finer. In addition, using expensive material such as a DNA sample, reagent, enzyme, etc. in large amount runs counter to reducing the cost for analysis and production. On the other hand, vibration means such as the above-described vibrator and ultrasonic oscillator has the difficulty of reducing the size thereof and, therefore, it is also difficult to apply that vibration means to the reaction cell that has been made smaller in size or finer in structure.

Also, even if using the above-described vibrator or ultrasonic oscillator for agitating the solution within the reaction cell, the internal solution becomes likely to get stagnated or come into a laminar flow. In a case where the solution within the reaction cell is in a state of being stagnated or being in a laminar flow, the reaction rate becomes likely to depend on a diffusion rate, with the result that the effect of promoting the reaction within the reaction cell using the above-described vibration means is small. Especially, in a case where the amount of the solution is small and the viscosity of the solution is relatively high, effective agitation becomes further difficult to perform. Further, in a case where the vibrator or the ultrasonic oscillator is employed, there is the inconvenience that cavitation becomes likely to occur and this damages the biopolymer in the solution.

The present invention has been made in view of the above-described problems and an object thereof is to provide a reaction cell which can be made small in size and which can enhance the agitation efficiency and realize the control of the reaction, and a method of using that reaction cell.

The reaction cell of the present invention is provided with a cell that has provided thereon a circumferential wall portion and a bottom portion so as to accommodate a relevant solution therein and with a piezoelectric/electrostrictive oscillator that is fixed to the outside surface of the circumferential wall portion, the bottom portion or a part of the bottom portion and that integrally vibrates.

In the reaction cell of the present invention, the piezoelectric/electrostrictive oscillator oscillates integrally with the circumferential wall portion or the bottom portion, thereby the solution is agitated. Therefore, with the device that is very small in size, it is possible to highly efficiently promote the progress of the reaction. Also, by controlling the vibration length of time of the piezoelectric/electrostrictive oscillator, the interval at which the vibration is performed, etc., it is possible to control the degree of the progress of the reaction of the solution, the reaction length of time, etc.

Preferably, the piezoelectric/electrostrictive oscillator is provided with electronic means for detection of its electric constant change. As the reaction proceeds, properties of the solution such as viscosity vary and, resultantly, the electric constant of the piezoelectric/electrostrictive oscillator changes. Therefore, by equipping the oscillator with means for detection of this electric constant, it is possible to determine the state of reaction of the solution. In this manner, it is possible to dynamically control the reaction of the solution.

Preferably, when $\Delta d$ represents an amplitude of the piezoelectric/electrostrictive oscillator and d represents a length in the vibration direction of the cell, the vibration of the piezoelectric/electrostrictive oscillator is set in the way of $0.00000 < \Delta d/d < 0.01$. If $0.000001 > \Delta d/d$, the effect of the vibration cannot be exhibited, whereas, if $\Delta d/d > 0.01$, the solution, especially in the case of a solution containing a biopolymer, the decompositions other than that intended to be made by the vibration, etc. become likely to occur. By setting the amplitude to be within the above-described range, more preferable promotion of the reaction is realized.

Preferably, the cell is constructed in a way in which the bottom portion of the cell is formed into a plurality of recesses so as to be partial cells and the plurality of partial cells are disposed in the form of a matrix. As a result of this, performing the reaction of the solution at multiple positions becomes possible and each of the partial cells can be provided with a piezoelectric/electrostrictive element. By simultaneously or individually controlling the operations of the piezoelectric/electrostrictive oscillators provided on the cells, it becomes possible to perform the control of the agitation, the control of the reaction, the detection of the status, etc. correspondingly in each partial cell. The piezoelectric/electrostrictive element can also be disposed on portions other than those of the bottom portion having formed therein those partial cells. In this case, the solution accommodated in a portion other than those where the partial cells are disposed can have its reaction controlled independently from the solution accommodated within the partial cells. Therefore, the degree of freedom for controlling the reaction is increased.

More preferably, a plurality of the piezoelectric/electrostrictive oscillators are disposed along the circumferential surface or bottom surface of the reaction cell and they are sequentially vibrated in the circumferential direction, or the amplitude and timing of that vibration are independently controlled. In a case where the solution within the reaction cell is not easily uniformly agitated, the vibration of a plurality of the piezoelectric/electrostrictive oscillators promotes uniform agitation.

More preferably, the circumferential wall portion and the bottom portion are constructed in the way of their being made of zirconia and integrally sintered. In a case where each of them is made of zirconia, the cell can have accommodated the solution therein so as to less attenuate the vibration of the piezoelectric/electrostrictive oscillator. In addition, zirconia has small reactability with raw materials of the piezoelectric/electrostrictive oscillator and, therefore, the deterioration of the zirconia does not occur, thereby an integrally formed cell can be realized. Incidentally, in general, zirconia can be sintered with an additive such as yttria so that a crystalline structure thereof can be made up of a mixture of tetragonal crystal, cubic crystal, and monoclinic crystal and thereby has a sufficiently high level of mechanical strength. In this case, the cell may be formed into a multilayer structure, a portion of which, especially the inside of the cell that contacts a water-soluble solution, has a higher proportion of the cubic crystal with a higher content of an additive such as yttria. By doing so, in addition to the merit that the mechanical strength of the cell is maintained, the occurrence of the crystalline metamorphosis of zirconia at the portion in contact with the solution can be prevented. Consequently, it is possible to realize the reaction cell, the durability of which has been more enhanced.

In place of zirconia, the cell may be made from optical transmissive ceramics. In a case where using the optical transmissive ceramics, the status of reaction of the solution can be detected by light. Also, the cell may be made into a hybrid structure wherein the circumferential wall portion is formed using ceramics and the bottom portion is formed using transparent glass or synthetic resin. Further, the cell may also be made into a structure wherein the circumferential wall portion and bottom portion are formed using transparent glass or synthetic resin and the piezoelectric/electrostrictive oscillator is adhered onto the circumferential wall or bottom portion. By having the cell integrally sintered with optical transmissive ceramics, the piezoelectric/electrostrictive oscillator can be sintered and formed directly on the cell. Also, by having the cell made up into a structure wherein the circumferential wall portion is made of ceramics and the bottom portion is made of transparent glass or synthetic resin, the following merits are obtained. Namely, peripheral portions of the cell can stably be produced employing a manufacturing method that is suitable for mass-production, such as green sheet lamination, sintering, etc. In addition, a combined structure with the transparent glass or synthetic resin as the bottom portion which is suitable for immobilizing biopolymer, etc. and detecting the status of the reaction through the use of a light can be realized. This enables providing a reaction cell that is inexpensive and has high performance. Also, by having the cell made up into a structure wherein the piezoelectric/electrostrictive oscillator is adhered onto the circumferential wall portion or the bottom portion, more options about a selection of the material applied to the circumferential wall portion or bottom portion are given. As a result, optimum selection of the material becomes possible from the biochemical point of view.

DETAILED DESCRIPTION OF THE INVENTION

Figure 1A:
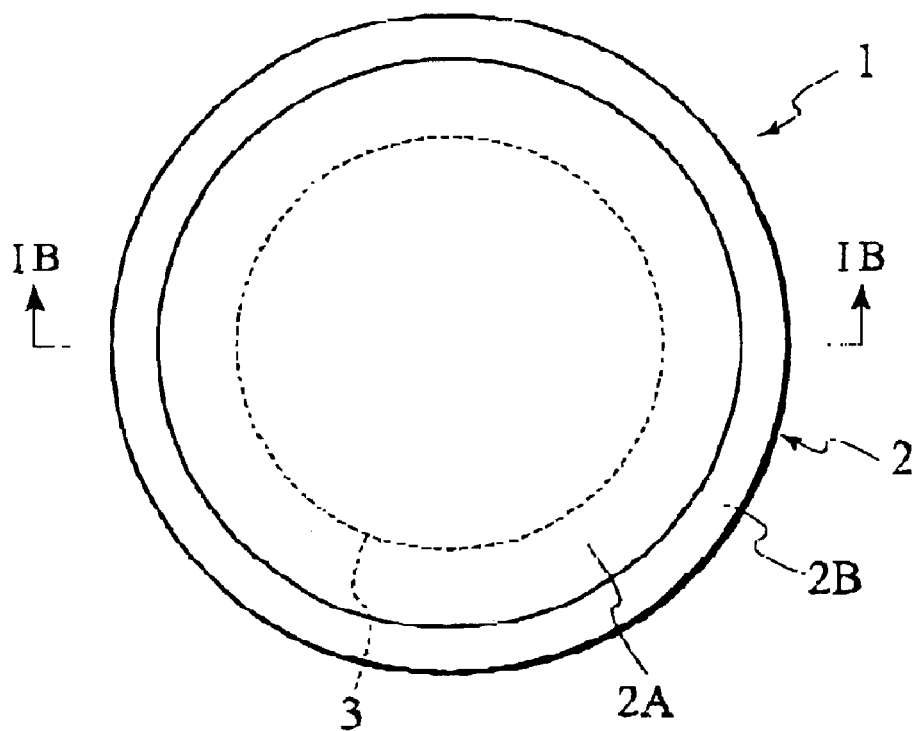
FIG. 1A is a plan view of a reaction cell according to a first embodiment of the present invention.

A reaction cell and a method of using it according to respective embodiments illustrated in the drawings will be described hereinafter.

[Reaction Cell]

FIRST EMBODIMENT

Figure 1B:
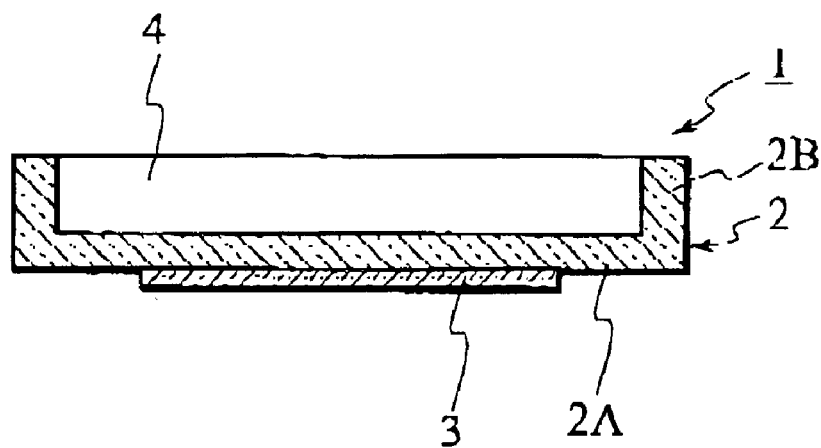
FIG. 1B is a sectional view of the reaction cell according to the first embodiment of the present invention, the section being shown taken along a line IB-IB of FIG. 1A.

A first embodiment of the present invention will be described with reference to FIGS. 1A and 1B.

A reaction cell 1 according to this embodiment comprises a vessel-like cell main body 2 and a circular piezoelectric/electrostrictive oscillator 3 which is provided on the underside (outside surface) of a bottom portion of the cell main body 2. It is to be noted that, although details of the piezoelectric/electrostrictive oscillator 3 are not illustrated in the drawings, the piezoelectric/electrostrictive oscillator 3 has a sandwiched structure wherein a dielectric material member is sandwiched between an upper electrode and a lower electrode. In the cell main body 2, a circular bottom plate portion 2A and a circumferential wall portion 2B which rises from a circumferential edge of the bottom plate portion 2A to thereby surround the bottom plate portion 2A are integrally formed using, for example, zirconia. In the reaction cell 1 having that structure, a space which is surrounded by the circumferential wall portion 2B on the bottom plate portion 2A constitutes a solution accommodation space 4. The piezoelectric/electrostrictive oscillator 3, as illustrated in FIG. 1A, is disposed and adhered on the underside of the bottom plate portion 2A concentrically with the bottom plate portion 2A. The diameter of the piezoelectric/electrostrictive oscillator 3 is set to be shorter than that of the bottom plate portion 2A. Incidentally, the diameter of the solution accommodation space of the reaction cell 1 can suitably be set to a value falling within a range of from several tens of μm to several tens of cm according to the kind of the solution or the purpose of detection thereof. Especially, when $\Delta d$ represents the amplitude of the vibration of the piezoelectric/electrostrictive oscillator 3 and d represents the length as viewed in the vibration direction, preferably, $0.000001 < \Delta d/d < 0.01$. If $0.000001 > \Delta d/d$, the effect of the vibration cannot be exhibited, whereas, if $\Delta d/d > 0.01$, the solution, especially in the case of its being a solution containing biopolymer, the decompositions other than that intended to be made by the vibration, etc. become likely to occur.

In the reaction cell 1 according to this embodiment, the piezoelectric/electrostrictive oscillator 3 is driven in a state where a solution is accommodated within the solution accommodation space 4. By doing so, the bottom plate portion 2A makes its deflection oscillation, whereby the vibration can be transmitted to the solution within the solution accommodation space 4. Incidentally, in a case where the frequency of the drive is sufficiently higher than the resonance frequency of the reaction cell 1 having accommodated therein the solution, or in a case where the rigidity of the bottom plate portion 2A is sufficiently high, the oscillation which has occurred from the piezoelectric/electrostrictive oscillator 3 is transmitted to the solution within the solution accommodation space 4 via the bottom plate portion 2A. And, it is arranged that, by the oscillation being transmitted to the solution, the solution be agitated, whereby a prescribed reaction of solution proceeds. Here, the oscillation of the piezoelectric/electrostrictive oscillator 3 is fine oscillation, and, therefore, agitation can be done without causing the occurrence of cavitation in the solution and, for example, without the three-dimensional structure such as a biopolymer being damaged.

Also, because the piezoelectric/electrostrictive oscillator 3 is used as the oscillation source, concurrent use of other chemical appliances such as heating means can easily be made.

Incidentally, the piezoelectric/electrostrictive oscillator 3 is connected to a drive control circuit via a wiring not illustrated so that the number of oscillations and the oscillation length of time and so forth may suitably be controlled.

Further, to the piezoelectric/electrostrictive oscillator 3 there is connected via a wiring (not illustrated) a signal generating/analyzing circuit. A voltage signal which excites feeble oscillation is applied thereto and there is detected a change in the electric constant which follows that oscillation. By doing so, it is possible to determine the specific gravity, viscosity, etc. of the solution. The status in which the reaction within the reaction cell 1 proceeds is detected as above by means of the viscosity and, by doing so, it is possible to automatically perform optimum oscillation in correspondence with the status of progress of the reaction. Detecting the change in the characteristic of the fluid in that way is described in, for example, Japanese Patent Application Laid-Open No. 8-201265. In this embodiment as well, the contents therein can be referred to.

SECOND EMBODIMENT

A second embodiment of the present invention will now be described with reference to FIGS. 2A and 2B.

A reaction cell 10 according to this embodiment comprises a vessel-like cell main body 11 and an annular piezoelectric/electrostrictive oscillator 12 which is provided on the underside of a bottom portion of the cell main body 11.

In the cell main body 11, a circular bottom plate portion 11A and a circumferential wall portion 11B which rises from a circumferential edge of the bottom plate portion 11A to thereby surround the bottom plate portion 11A are integrally formed using, for example, optical transmissive alumina. In the reaction cell 10 having that structure, a space which is surrounded by the circumferential wall portion 11B on the bottom plate portion 11A constitutes a solution accommodation space 13. Incidentally, the diameter of the solution accommodation space 13 of the reaction cell 10 can suitably be set to a value falling within a range of from several tens of μm to several tens of cm according to the kind of the solution or the purpose of detection thereof. In this embodiment as well, for the same reason as stated above, when Δd represents the amplitude of the oscillation of the piezoelectric/electrostrictive oscillator 12 and d represents the length as viewed in the oscillation direction, preferably, $0.000001 < \Delta d/d < 0.01$.

Figure 2A:
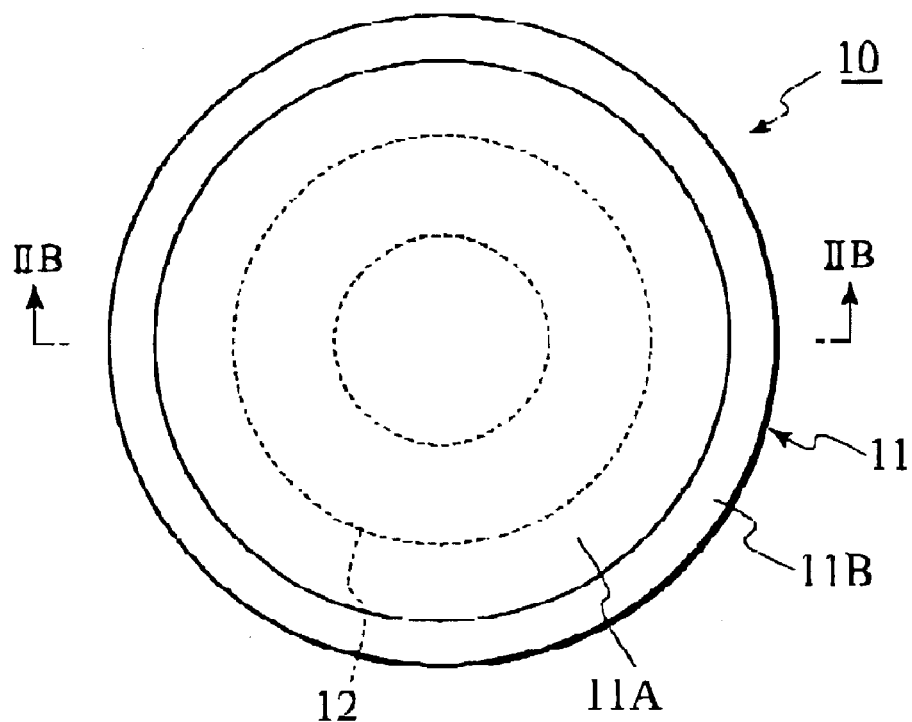
FIG. 2A is a plan view of a reaction cell according to a second embodiment of the present invention.
Figure 2B:
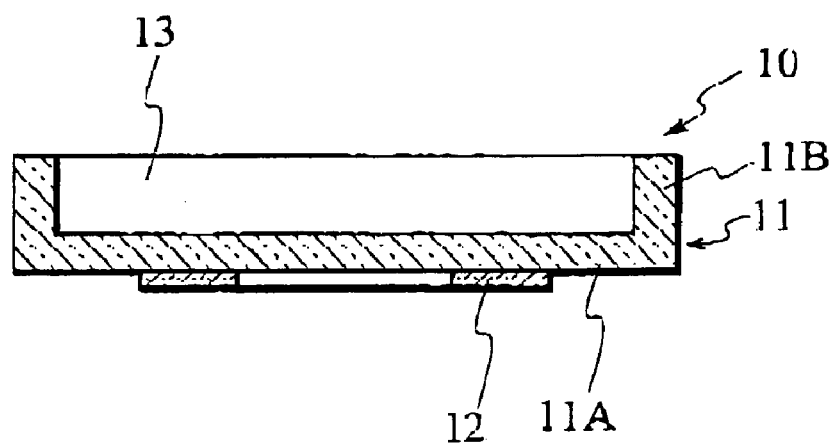
FIG. 2B is a sectional view of the reaction cell according to the second embodiment of the present invention, the section being shown taken along a line IIB-IIB of FIG. 2A.

The piezoelectric/electrostrictive oscillator 12, as illustrated in FIG. 2A, is disposed and adhered on the underside of the bottom plate portion 11A concentrically with the bottom plate portion 11A. The maximum diameter of the piezoelectric/electrostrictive oscillator 12 is set to be shorter than that of the bottom plate portion 11A. Since as described above the piezoelectric/electrostrictive oscillator 12 is annular, the central part of the bottom plate 11A constitutes an area where the piezoelectric/electrostrictive oscillator 12 does not exist. For this reason, by setting the thickness of the bottom plate portion 11A to be at a value permitting this portion 11A to have optical transmissivity, or by forming the bottom plate portion 11A using a material having good optical transmissivity, monitoring the status of the solution at the central part of the bottom plate portion 11A becomes possible by measuring the optical transmittance at the central part.

In the reaction cell 10, as well, according to this embodiment, when driving the piezoelectric/electrostrictive oscillator 12 in a state where the solution is accommodated within the solution accommodation space 13, the bottom plate portion 11A makes its deflection oscillation, and this oscillation is transmitted to the solution within the solution accommodation space 13. Or, via the bottom plate portion 11A, the oscillation which has occurred in the piezoelectric/electrostrictive oscillator 12 can be transmitted to the solution within the solution accommodation space 13. And, it is arranged that, by the oscillation being transmitted to the solution, the solution be agitated whereby the reaction of the solution is promoted.

THIRD EMBODIMENT

A third embodiment of the present invention will be described with reference to FIGS. 3A and 3B.

A reaction cell 20 according to this embodiment comprises a vessel-like cell main body 21 and a circular piezoelectric/electrostrictive oscillator 22 which is provided within the cell main body 21. It is to be noted that, although the details of the piezoelectric/electrostrictive oscillator 22 are not illustrated, the piezoelectric/electrostrictive oscillator 22 has a sandwiched structure wherein a dielectric material member is sandwiched between an upper electrode and a lower electrode. The cell main body 21 is constructed of a circular bottom plate portion 21A and a circumferential wall portion 21B which rises from a circumferential edge of the bottom plate portion 21A to thereby surround the bottom plate portion 21A. And the bottom plate portion 21A and the circumferential wall portion 21B are integrally formed, the bottom plate portion 21A being formed of, for example, optical transmissive alumina and the circumferential wall portion 21B being formed of, for example, zirconia. In the reaction cell 20 having that structure, a space which is surrounded by the circumferential wall portion 21B on the bottom plate portion 21A constitutes a solution accommodation space 23.

Figure 3A:
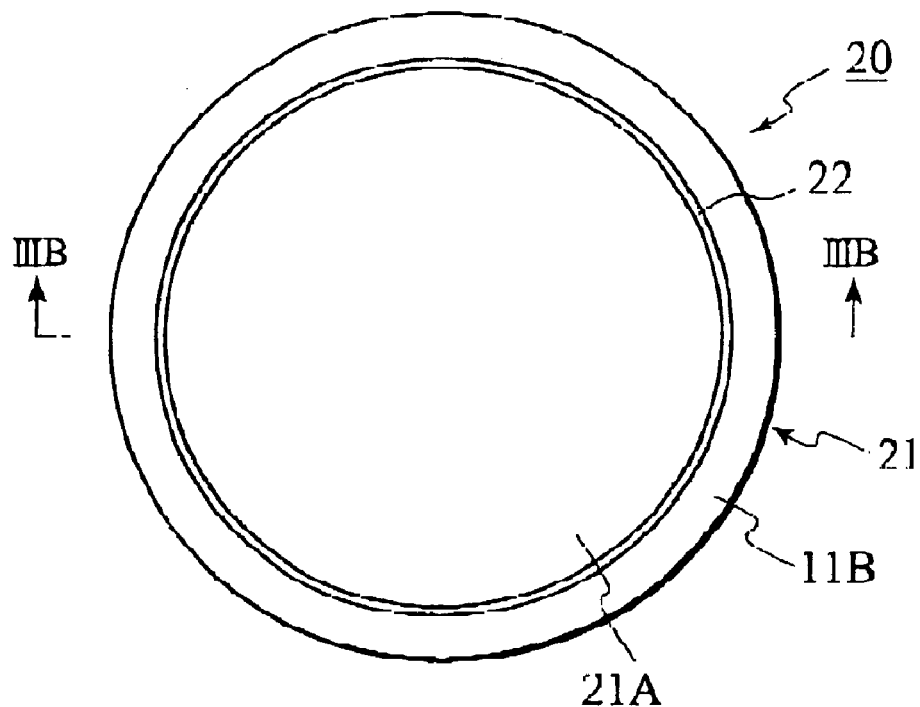
FIG. 3A is a plan view of a reaction cell according to a third embodiment of the present invention.
Figure 3B:
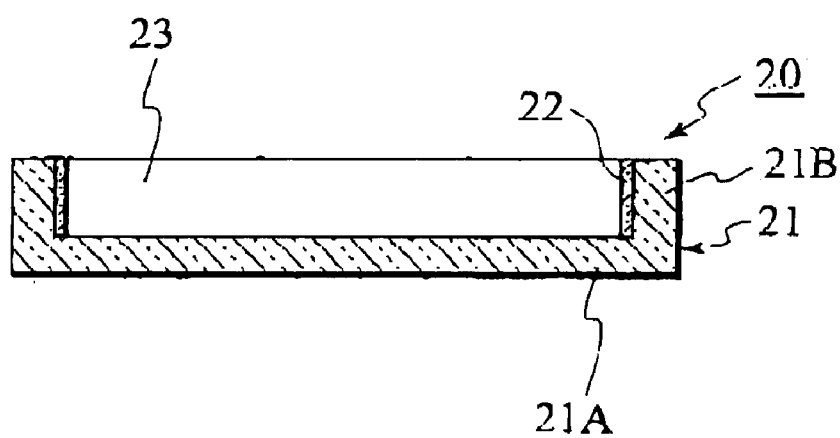
FIG. 3B is a sectional view of the reaction cell according to the third embodiment of the present invention, the section being shown taken along a line IIIB-IIIB of FIG. 3A.

The piezoelectric/electrostrictive oscillator 22, as illustrated in FIG. 3A, is disposed and adhered along the inside surface of the circumferential wall portion 21B in the way of its circumferentially extending. Like that, in this embodiment as well, it becomes possible to detect the status of reaction of the internal solution using a light by constructing the bottom plate portion 21A using a structure, or material, having optical transmissivity. Incidentally, in this embodiment as well, the diameter of the solution accommodation space 23 of the reaction cell 20 can suitably be set according to the kind of the solution or the purpose of detection thereof.

In the reaction cell 20 according to this embodiment, by driving the piezoelectric/electrostrictive oscillator 22 in a state where the solution is accommodated within the solution accommodation space, it is possible to transmit the oscillation which has occurred in the piezoelectric/electrostrictive oscillator 22 to the solution within the solution accommodation space 23 directly, or via the bottom plate portion 21A. And, it is arranged that, by the oscillation being transmitted to the solution, the solution be agitated whereby a prescribed reaction of solution is promoted.

Incidentally, the piezoelectric/electrostrictive oscillator 22 is connected to a drive control circuit via a wiring not illustrated so that the number of oscillations and the oscillation length of time and so forth may suitably be controlled. And, on the surface of the piezoelectric/electrostrictive oscillator inside the cell there is applied over an upper electrode thereof a waterproof coat made of resin, etc. in the way in which the waterproof coat covers the oscillator as a whole.

FOURTH EMBODIMENT

Figure 4A:
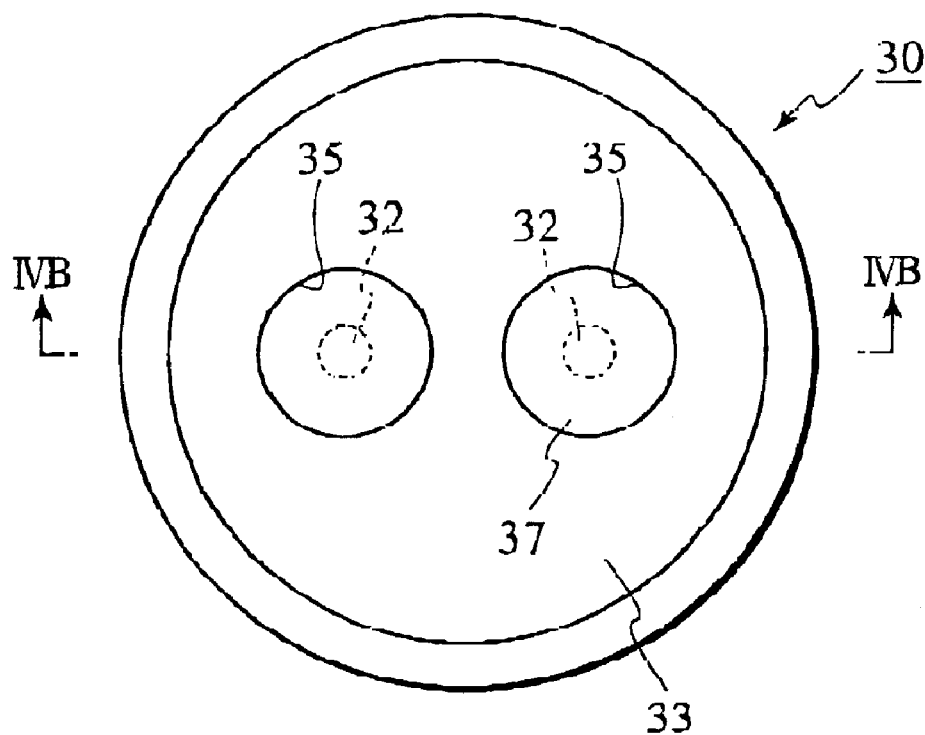
FIG. 4A is a plan view of a reaction cell according to a fourth embodiment of the present invention.
Figure 4B:
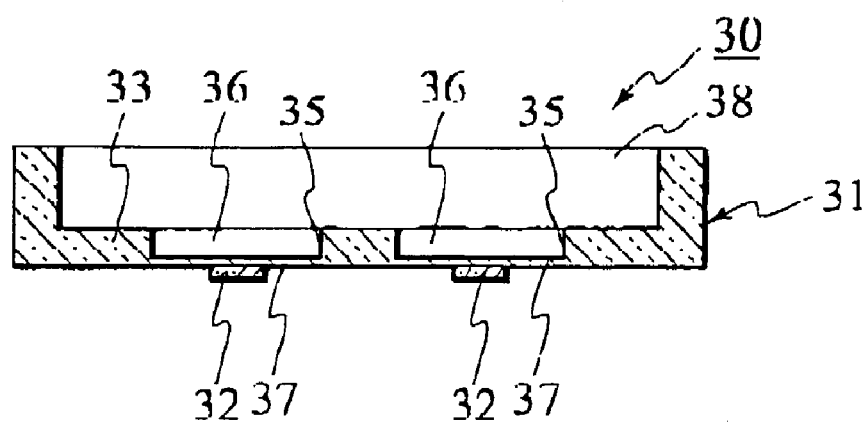
FIG. 4B is a sectional view of the reaction cell according to the fourth embodiment of the present invention, the section being shown taken along a line IVB-IVB of FIG. 4A.

A fourth embodiment of the present invention will be described with reference to FIGS. 4A and 4B.

A reaction cell 30 according to this embodiment comprises a vessel-like cell main body 31 and a pair of piezoelectric/electrostrictive oscillators 32 provided on the underside (outside surface) of the cell main body 31. The cell main body 31 is constructed of a circular bottom plate portion 33, the thickness of which is relatively great, and a circumferential wall portion 34 which rises from the circumferential edge of the bottom plate portion 33 and which surrounds the bottom plate portion 33, the both portions 33 and 34 being integrally formed using, for example, zirconia.

In the upper surface of the bottom plate portion 33 there are formed a pair of U-shaped recesses 35 which, when viewed from above them, are circular in the way in which they sandwich the central part of the bottom portion 33. These U-shaped recesses 35 each form a solution accommodation small space 36 for accommodating therein a relevant solution. And, the above-described piezoelectric/electrostrictive oscillator 32 is disposed and adhered on the central part of the underside of a relatively thin bottom plate 37 of the corresponding U-shaped recess 35. The reaction cell 30 having such structure has the solution accommodation small space 36 within each U-shaped recess 35 and a solution accommodation large space 38 which is surrounded by the circumferential wall portion 34 on the bottom plate portion 33. The above-described piezoelectric/electrostrictive oscillator 32 is circular, the diameter of which is smaller than that of the bottom plate 37. Incidentally, the solution accommodation large space 38 in the reaction cell 30 can suitably be set to a value falling within a range of from several tens of μm to several tens of cm according to the kind of the solution or the purpose of detection thereof.

The reaction cell 30 according to this embodiment may be used in a state where the relevant solution is accommodated within only the solution accommodation small space 36 alone, or may be used in a state where the solution is accommodated within the solution accommodation large space 38. And, by driving the piezoelectric/electrostrictive oscillator 32, the oscillation which has occurred in the piezoelectric/electrostrictive oscillator 32 can be transmitted to the solution within the solution accommodation small space 36 and the solution within the solution accommodation large space 38. And, because the oscillation is transmitted to the solution, the solution is agitated and a prescribed reaction of the solution is promoted. Incidentally, by individually oscillation controlling the solution accommodation small space 36, the reaction of the solution in each small space (cavity) is optimized, with the result that the reaction within the solution accommodation large space 38 can also be controlled to a desired status of reaction.

Incidentally, in the reaction cell 30, as well, according to this embodiment, the piezoelectric/electrostrictive oscillator 32 is connected to a drive control circuit via a wiring not illustrated so that the number of oscillations and the oscillation length of time and so forth may suitably be controlled.

FIFTH EMBODIMENT

Figure 5A:
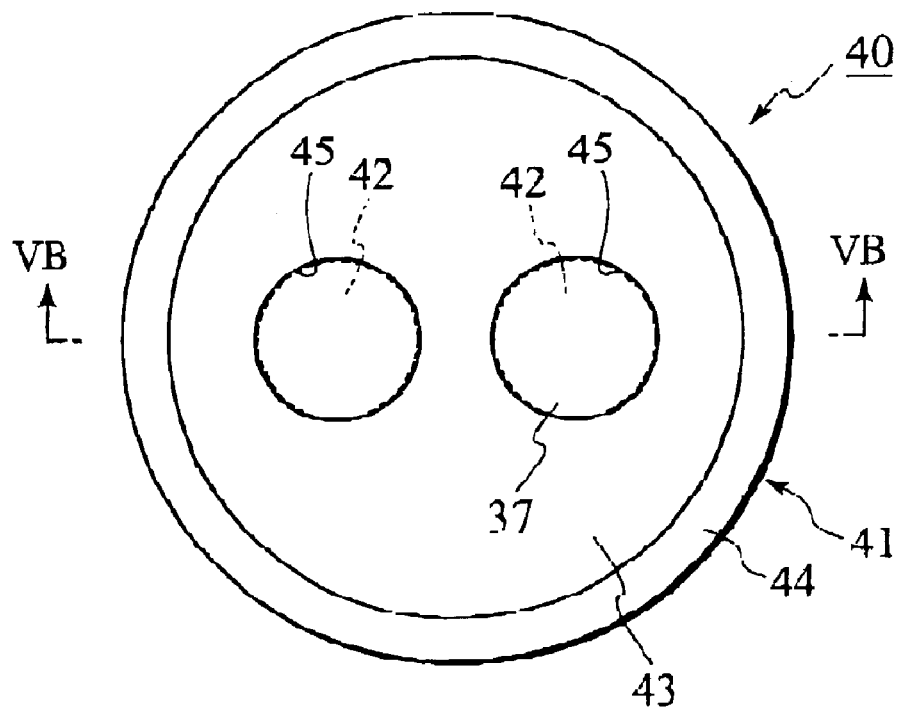
FIG. 5A is a plan view of a reaction cell according to a fifth embodiment of the present invention.
Figure 5B:
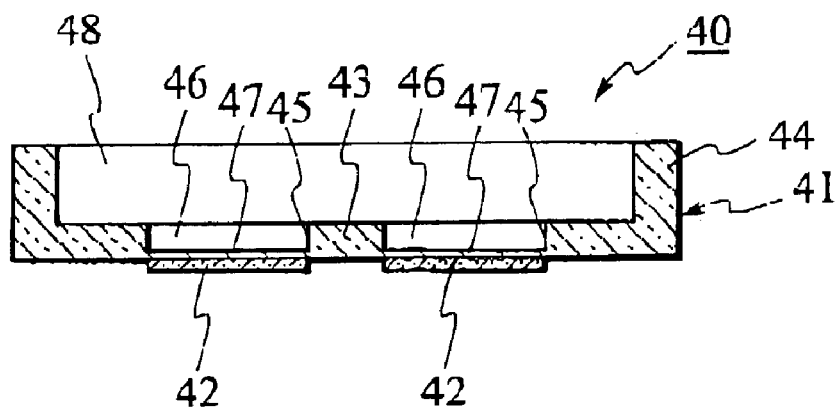
FIG. 5B is a sectional view of the reaction cell according to the fifth embodiment of the present invention, the section being shown taken along a line VB-VB of FIG. 5A.

A fifth embodiment of the present invention will be described with reference to FIGS. 5A and 5B.

A reaction cell 40 according to this embodiment comprises a vessel-like cell main body 41 and a pair of piezoelectric/electrostrictive oscillators 42 provided on the underside (outside surface) of the bottom portion of the cell main body 41. The cell main body 41 is constructed of a circular bottom plate portion 33, the thickness of which is relatively great, and a circumferential wall portion 44 which rises from the circumferential edge of the bottom plate portion 43 and which surrounds the bottom plate portion 43, the both portions 43 and 44 being integrally formed using, for example, zirconia.

In the upper surface of the bottom plate portion 43 there are formed a pair of U-shaped recesses 45 which, when viewed from above them, are circular in the way in which they sandwich the central part of the bottom portion 43. These U-shaped recesses 45 each form a solution accommodation small space 46 for accommodating therein a relevant solution. And, the above-described piezoelectric/electrostrictive oscillator 42 is disposed and adhered on the central part of the underside of a relatively thin bottom plate 47 of the corresponding U-shaped recess 45. The reaction cell 40 having such structure has the solution accommodation small space 46 within each U-shaped recess 45 and a solution accommodation large space 48 which is surrounded by the circumferential wall portion 44 on the bottom plate portion 43. The above-described piezoelectric/electrostrictive oscillator 42 is circular, the diameter of which is equal to that of the bottom plate 47. Incidentally, the diameter of the solution accommodation large space 48 in the reaction cell 40 can suitably be set to a value falling within a range of from several tens of μm to several tens of cm according to the kind of the solution or the purpose of detection thereof.

The reaction cell 40 according to this embodiment may be used in a state where the relevant solution is accommodated within only the solution accommodation small space 46 alone, or may be used in a state where the solution is accommodated within the solution accommodation large space 48. And, by driving the piezoelectric/electrostrictive oscillator 42, the oscillation which has occurred in the piezoelectric/electrostrictive oscillator 42 can be transmitted to the solution within the solution accommodation small space 46 and the solution within the solution accommodation large space 48. And, because the oscillation is transmitted to the solution, the solution is agitated and a prescribed reaction of the solution is promoted. Incidentally, since the piezoelectric/electrostrictive oscillator 42 has a diameter that is equal to the diameter of the bottom plate 47, the oscillation within the U-shaped recess 45 can be uniformly transmitted to the solution.

Incidentally, in the reaction cell 40, as well, according to this embodiment, the piezoelectric/electrostrictive oscillator 42 is connected to a drive control circuit via a wiring not illustrated so that the number of oscillations and the oscillation length of time and so forth may suitably be controlled.

SIXTH EMBODIMENT

Figure 6A:
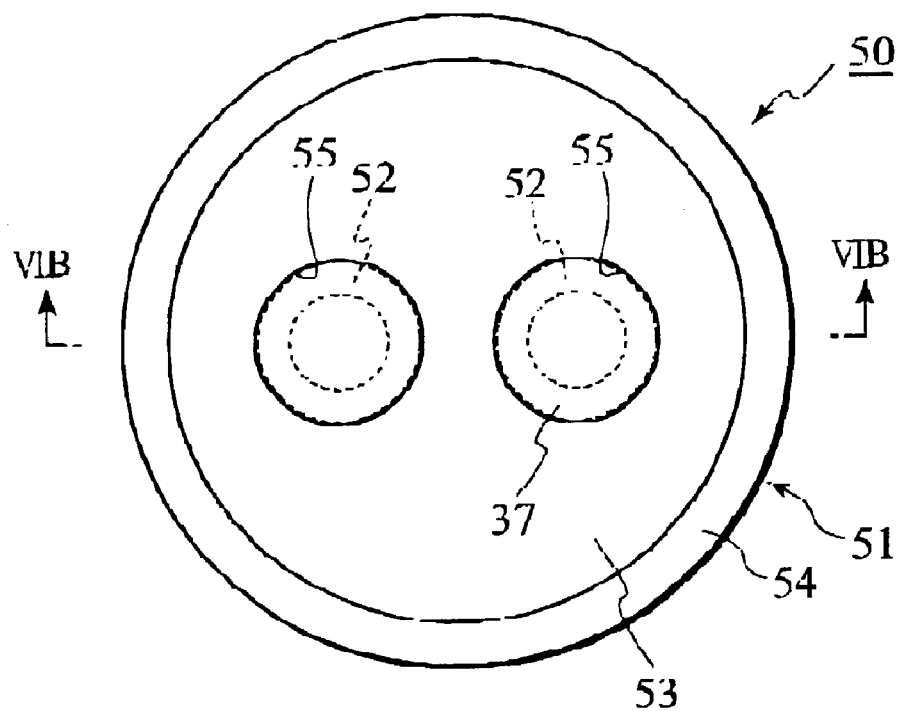
FIG. 6A is a plan view of a reaction cell according to a sixth embodiment of the present invention.
Figure 6B:
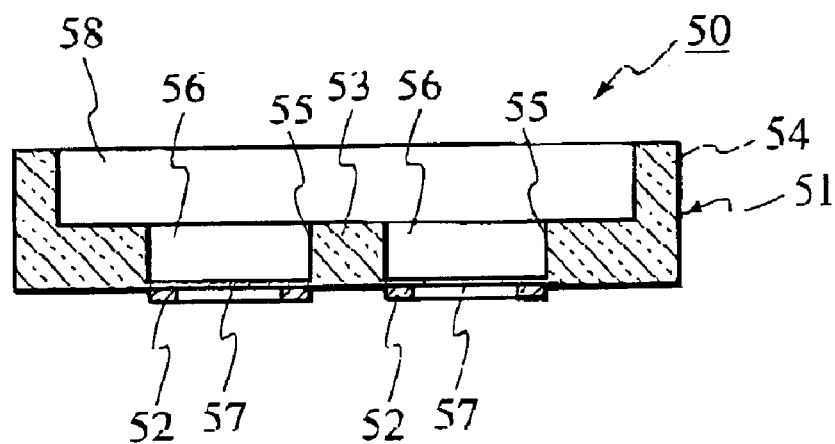
FIG. 6B is a sectional view of the reaction cell according to the sixth embodiment of the present invention, the section being shown taken along a line VIB-VIB of FIG. 6A.

A sixth embodiment of the present invention will be described with reference to FIGS. 6A and 6B.

A reaction cell 50 according to this embodiment comprises a vessel-like cell main body 51 and a pair of annular piezoelectric/electrostrictive oscillators 52 provided on the underside (outside surface) of the bottom portion of the cell main body 51. The cell main body 51 is constructed of a circular bottom plate portion 53, the thickness of which is relatively great, and a circumferential wall portion 54 which rises from the circumferential edge of the bottom plate portion 53 and which surrounds the bottom plate portion 53, the both portions 53 and 54 being integrally formed using, for example, zirconia.

In the upper surface of the bottom plate portion 53 there are formed a pair of U-shaped recesses 55 which, when viewed from above them, are circular in the way in which they sandwich the central part of the bottom portion 53 therebetween. These U-shaped recesses 55 each form a solution accommodation small space 56 for accommodating therein a relevant solution. And, the above-described piezoelectric/electrostrictive oscillator 52 is disposed and adhered on the central part of the underside of a thin bottom plate 57 of the corresponding U-shaped recess 55. The reaction cell 50 having such structure has the solution accommodation small space 56 within each U-shaped recess 55 and a solution accommodation large space 58 which is surrounded by the circumferential wall portion 54 on the bottom plate portion 53. The above-described piezoelectric/electrostrictive oscillator 52 is annular the maximum diameter of which is equal to that of the bottom plate 57.

Incidentally, the diameter of the solution accommodation large space 58 in the reaction cell 50 can suitably be set to a value falling within a range of from several tens of μm to several tens of cm according to the kind of the solution or the purpose of detection thereof. In the reaction cell 50 according to this embodiment, in order to make great the depth of the U-shaped recess 55, the thickness of the bottom plate portion 53 is set to have a great thickness. Also, the thickness of the bottom plate 57 is set to have a small thickness so as to permit a light to pass therethrough. And, since the piezoelectric/electrostrictive oscillator 52 does not exist at the central part of the bottom plate 57, it is possible to detect the change in the optical transmittance of the solution due to the progress of the solution within the U-shaped recess 55, or to detect the luminous reaction of the solution. In addition, the portion where the piezoelectric/electrostrictive oscillator 52 is designed to have no optical transmissivity. Therefore, in a case where detecting the luminous reaction, that construction is advantageous for decreasing the crosstalk of light which is emitted from each U-shaped recess 55.

The reaction cell 50 according to this embodiment may also be used in a state where the relevant solution is accommodated within only the solution accommodation small space 56 alone, or may be used in a state where the solution is accommodated within the solution accommodation large space 58. And, by driving the piezoelectric/electrostrictive oscillator 52, the oscillation which has occurred in the piezoelectric/electrostrictive oscillator 52 can be transmitted to the solution within the solution accommodation small space 56 and the solution within the solution accommodation large space 58 via the bottom plate 57. And, because the oscillation is transmitted to the solution, the solution is agitated and a prescribed reaction of the solution is promoted.

Incidentally, in the reaction cell 50, as well, according to this embodiment, the piezoelectric/electrostrictive oscillator 52 is connected to a drive control circuit via a wiring not illustrated so that the number of oscillations and the oscillation length of time and so forth may suitably be controlled.

SEVENTH EMBODIMENT

Figure 7A:
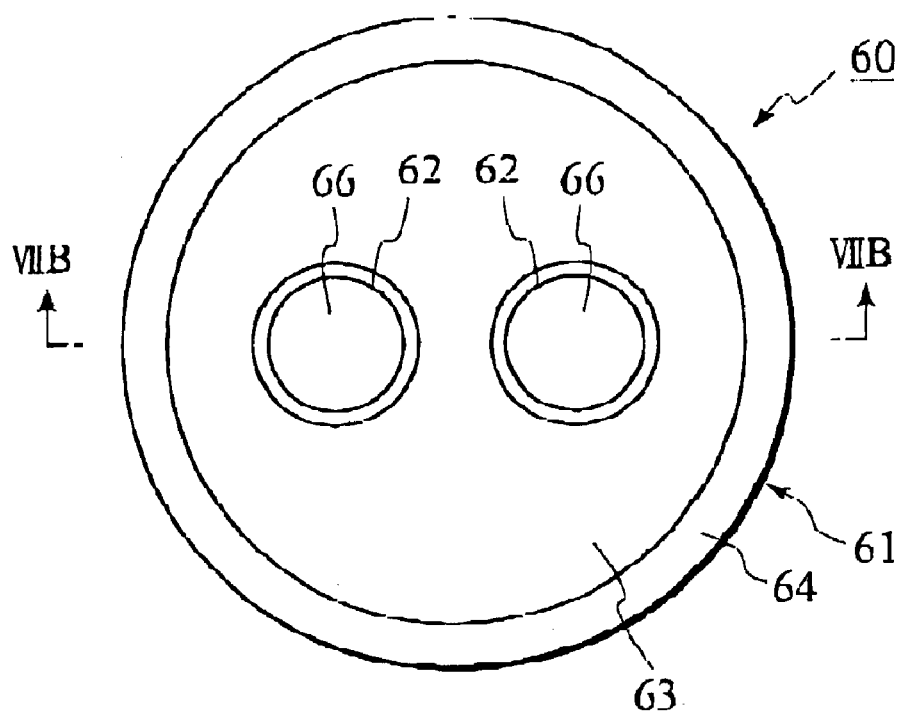
FIG. 7A is a plan view of a reaction cell according to a seventh embodiment of the present invention.
Figure 7B:
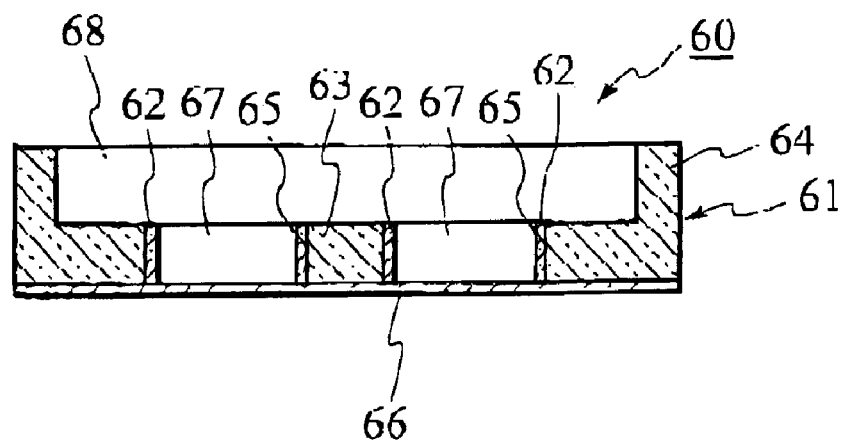
FIG. 7B is a sectional view of the reaction cell according to the seventh embodiment of the present invention, the section being shown taken along a line VIIB-VIIB of FIG. 7A.

A seventh embodiment of the present invention will be described with reference to FIGS. 7A and 7B.

A reaction cell 60 according to this embodiment comprises a vessel-like cell main body 61 and a pair of annular piezoelectric/electrostrictive oscillators 62 provided within the cell main body 61. The cell main body 61 is constructed of a circular bottom plate portion 63, the thickness of which is great, and a circumferential wall portion 64 which rises from the circumferential edge of the bottom plate portion 63 and which surrounds the bottom plate portion 63, the both portions 63 and 64 being integrally formed using, for example, zirconia.

In the bottom plate portion 63 there are formed a pair of circular holes 65 in the way in which they sandwich the central part of the bottom portion 63 therebetween. These circular holes 65 each have formed along their inner-circumferential wall surfaces the above-described piezoelectric/electrostrictive oscillator 62. On the underside of the bottom plate portion 63, over its entire surface, there is integrally fixedly provided a transparent plate 66 consisting of, for example, a transparent glass. Accordingly, the through-holes of the piezoelectric/electrostrictive oscillator 62 and the transparent plate 66 constitute a solution accommodation small space 67 for accommodating therein a relevant solution. Since the bottom portion of the solution accommodation small space 67 is formed of the transparent plate 66 in the reaction cell 60 according to this embodiment, it becomes possible to grasp the status of reaction of the internal solution by measuring the optical transmittance and luminous reaction and so forth. In addition, since the portion where the thick bottom plate portion 63 exists is formed of zirconia having no optical transmissivity and, therefore, in a case where detecting the luminous reaction, that construction is advantageous for decreasing the crosstalk of light emitted from the solution accommodation small space 67.

The reaction cell 60 having such structure has the solution accommodation small space 67 and a solution accommodation large space 68 which is surrounded by the circumferential wall portion 64 on the bottom plate portion 63. The diameter of the solution accommodation large space 68 in the reaction cell 60 can suitably be set to a value falling within a range of from several tens of μm to several tens of cm according to the kind of the solution or the purpose of detection thereof.

The reaction cell 60 according to this embodiment may also be used in a state where the relevant solution is accommodated within only the solution accommodation small space 67 alone, or may be used in a state where the solution is accommodated within the solution accommodation large space 68. And, by driving the piezoelectric/electrostrictive oscillator 62, the oscillation which has occurred in the piezoelectric/electrostrictive oscillator 62 can be transmitted directly to the solution within the solution accommodation small space 67 and the solution within the solution accommodation large space 68. And, by because the oscillation is transmitted directly to the solution, the solution is reliably agitated and a prescribed reaction of the solution is promoted.

Incidentally, in the reaction cell 60, as well, according to this embodiment, the piezoelectric/electrostrictive oscillator 62 is connected to a drive control circuit via a wiring not illustrated so that the number of oscillations and the oscillation length of time and so forth may suitably be controlled.

EIGHTH EMBODIMENT

Figure 8A:
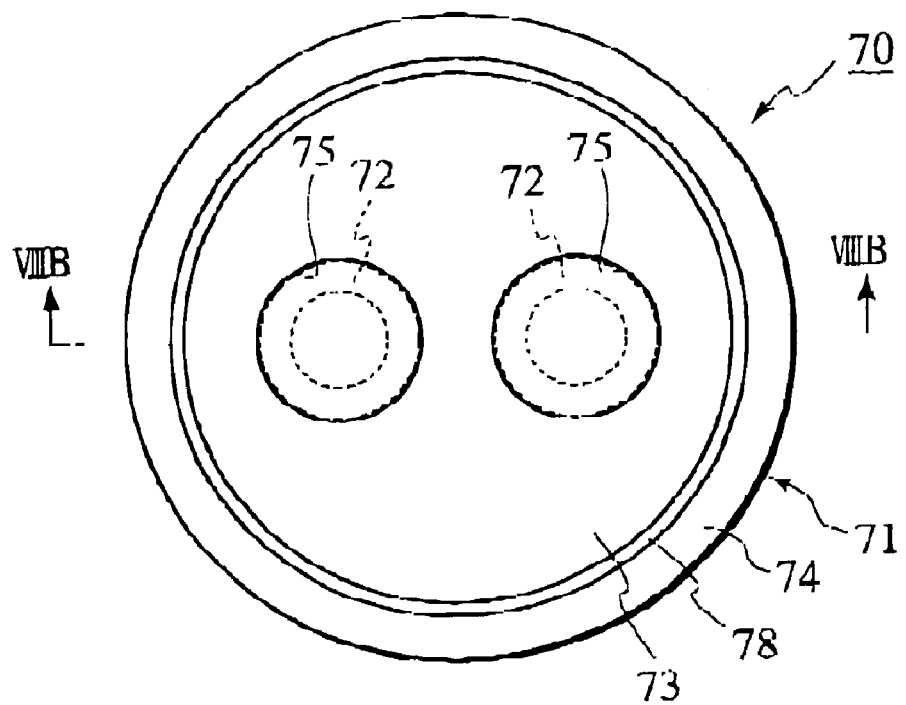
FIG. 8A is a plan view of a reaction cell according to an eighth embodiment of the present invention.
Figure 8B:
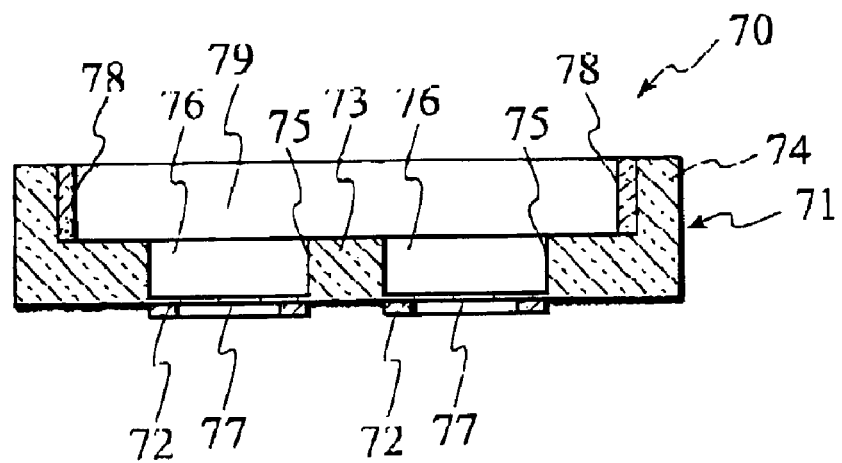
FIG. 8B is a sectional view of the reaction cell according to the eighth embodiment of the present invention, the section being shown taken along a line VIIIB-VIIIB of FIG. 8A.

An eighth embodiment of the present invention will be described with reference to FIGS. 8A and 8B.

A reaction cell 70 according to this embodiment comprises a vessel-like cell main body 71 and a pair of annular piezoelectric/electrostrictive oscillators 72 provided on the underside (outside surface) of the bottom portion of the cell main body 71 and an annular second piezoelectric/electrostrictive oscillator 78 provided within the cell main body 71. The cell main body 71 is constructed of a circular bottom plate portion 73, the thickness of which is relatively great, and that, when viewed from above the cell main body, is circular and a circumferential wall portion 74 rises from and surrounds the circumferential edge of the bottom plate portion 73, the both portions 73 and 74 being integrally formed using, for example, zirconia. The second piezoelectric/electrostrictive oscillator 78 is formed in such a way that it circumferentially extends along the inner-circumferential surface of the circumferential wall portion 74.

In the upper surface of the bottom plate portion 73 there are formed a pair of U-shaped recesses 75 which, when viewed from above them, are circular in the way in which they sandwich the central part of the bottom portion 73 therebetween. These U-shaped recesses 75 each form a solution accommodation small space 76 for accommodating therein a relevant solution. And, the above-described piezoelectric/electrostrictive oscillator 72 is disposed and adhered on the underside of a thin bottom plate 77 of the corresponding U-shaped recess 75.

The first piezoelectric/electrostrictive oscillator 72 is in the form of an annulus and has a maximum diameter equal to the diameter of the bottom plate 77.

Incidentally, the diameter of the solution accommodation large space 79 in the reaction cell 70 can suitably be set to a value falling within a range of from several tens of μm to several tens of cm according to the kind of the solution or the purpose of detection thereof. In the reaction cell 70 according to this embodiment, in order to make great the depth of the U-shaped recess 75, the thickness of the bottom plate portion 73 is set to have a great thickness. Also, the thickness of the bottom plate 77 is set to have a small thickness so as to permit a light to pass therethrough. And, since the first piezoelectric/electrostrictive oscillator 72 does not exist at the central part of the bottom plate 77, it is possible to detect the status of solution within the U-shaped recess 75 by measuring the change in the optical transmittance of the solution.

The reaction cell 70 according to this embodiment may also be used in a state where the relevant solution is accommodated within only the solution accommodation small space 76 alone, or may be used in a state where the solution is accommodated within the solution accommodation large space 79. And, by driving the first piezoelectric/electrostrictive oscillator 72, the bottom plate 77 makes its deflection oscillation whereby this oscillation can be transmitted to the solution within the solution accommodation small space 76. Also, by driving the second piezoelectric/electrostrictive oscillator 78, the oscillation can be transmitted directly to the solution within the solution accommodation large space 79. And, because the oscillation is transmitted to the solution, the solution is agitated and a prescribed reaction of the solution is promoted.

Incidentally, in the reaction cell 70, as well, according to this embodiment, the first and second piezoelectric/electrostrictive oscillators 72 and 78 are each connected to a drive control circuit via a wiring (not illustrated) so that the number of oscillations and the oscillation length of time and so forth may suitably be controlled. And, by adjusting the driving timing, amplitude, etc. of each of the first and second piezoelectric/electrostrictive oscillator, finer agitation of the solution and finer control and promotion of the reaction become possible.

NINTH EMBODIMENT

Figure 9A:
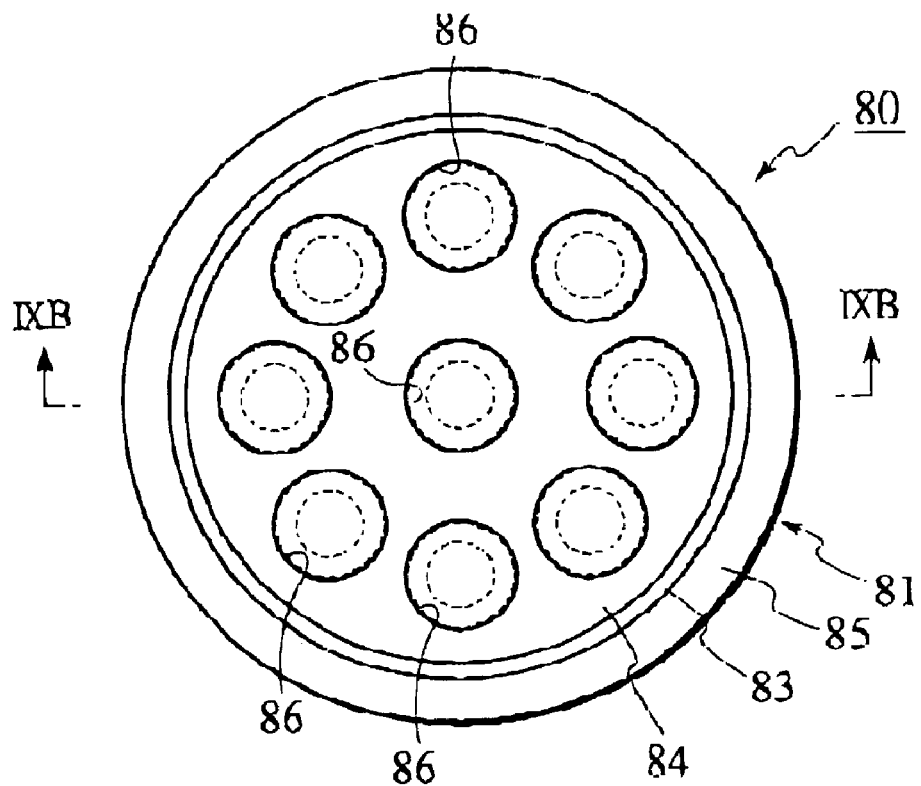
FIG. 9A is a plan view of a reaction cell according to a ninth embodiment of the present invention.
Figure 9B:
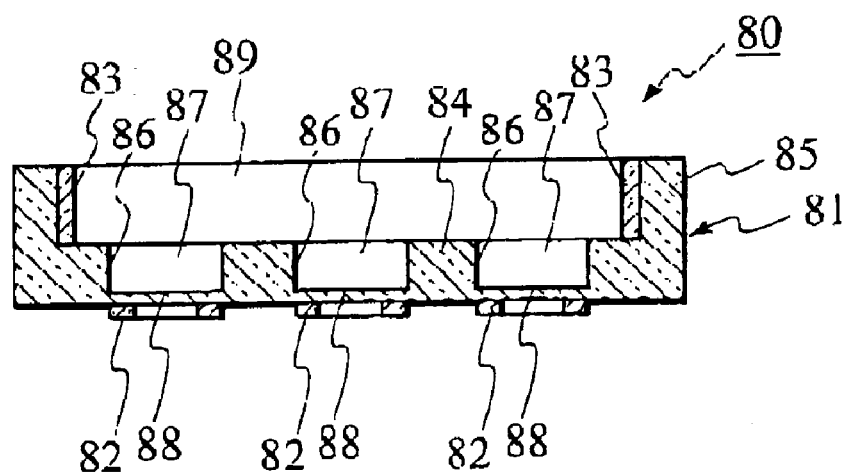
FIG. 9B is a sectional view of the reaction cell according to the ninth embodiment of the present invention, the section being shown taken along a line IXB-IXB of FIG. 9A.

A ninth embodiment of the present invention will be described with reference to FIGS. 9A and 9B.

A reaction cell 80 comprises a vessel-like cell main body 81 and a plurality of first piezoelectric/electrostrictive oscillators 82 provided on the underside (outside surface) of the bottom portion of the cell main body 81 and a second annular second piezoelectric/electrostrictive oscillator 83 provided within the cell main body 81. The cell main body 81 is constructed of a circular bottom plate portion 84, the thickness of which is relatively great and when viewed from above the cell main body, is circular and a circumferential wall portion 85 rises from and surrounds the circumferential edge of the bottom plate portion 84, the both portions 84 and 85 being integrally formed using, for example, zirconia. The second piezoelectric/electrostrictive oscillator 83 is formed in such a way that it circumferentially extends along the inner-circumferential surface of the circumferential wall portion 85. And, the space which is surrounded by the circumferential wall portion 85 on the bottom plate portion 84 constitutes a solution accommodation space 89.

In the upper surface of the bottom plate portion 84 there are formed at the central part of the bottom plate portion 84 and in the neighborhood of it a plurality of U-shaped recesses 86. This plurality of U-shaped recesses 86, when viewed from above them, are circular and these U-shaped recesses 86 each form a solution accommodation small space 87 for accommodating therein a relevant solution. And, the above-described first piezoelectric/electrostrictive oscillator 82 is disposed and adhered on the underside of a thin bottom plate 88 of the corresponding U-shaped recess 86. Incidentally, the first piezoelectric/electrostrictive oscillator 82 is in the form of an annulus and has a maximum diameter substantially equal to the diameter of the bottom plate 88.

Incidentally, the diameter of the solution accommodation large space 89 in the reaction cell 80 can suitably be set according to the kind of the solution or the purpose of detection thereof. In the reaction cell 80 according to this embodiment, in order to make great the depth of the U-shaped recess 86, the thickness of the bottom plate portion 84 is set to have a great thickness.

Also, the thickness of the bottom plate 88 is set to have a small thickness so as to permit a light to pass therethrough. And, since the first piezoelectric/electrostrictive oscillator 82 does not exist at the central part of the bottom plate 88, it is possible to detect the status of solution within the U-shaped recess 86 by measuring the optical transmittance through the bottom plate 88.

The reaction cell 80 according to this embodiment may also be used in a state where the relevant solution is accommodated within only the solution accommodation small space 87 alone, or may be used in a state where the solution is accommodated within the solution accommodation large space 89. And, by driving the first piezoelectric/electrostrictive oscillator 82, which causes the deflection oscillation of each of the plurality of bottom plates 88, the oscillation can be transmitted to the solution within the solution accommodation small space 87. Also, by driving the second piezoelectric/electrostrictive oscillator 83, the oscillation can be transmitted directly to the solution within the solution accommodation large space 89. And, because the oscillation is transmitted to the solution, the solution is agitated and a prescribed reaction of the solution is promoted.

Incidentally, in the reaction cell 80, as well, according to this embodiment, the first and second piezoelectric/electrostrictive oscillators 82 and 83 are each connected to a drive control circuit via a wiring (not illustrated) so that the number of oscillations and the oscillation length of time and so forth may suitably be controlled.

TENTH EMBODIMENT

Figure 10A:
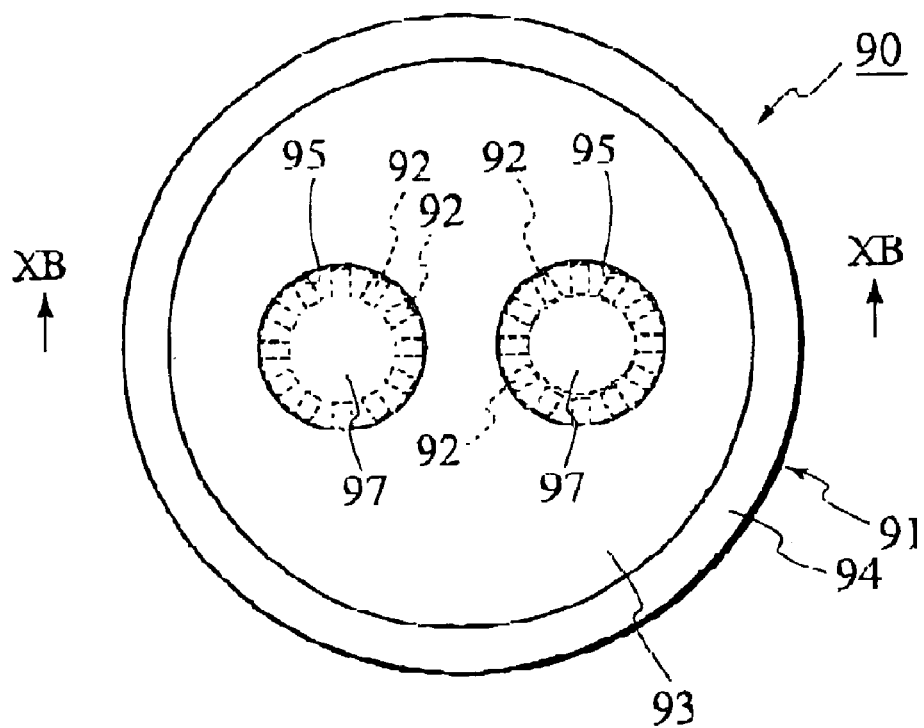
FIG. 10A is a plan view of a reaction cell according to a tenth embodiment of the present invention.
Figure 10B:
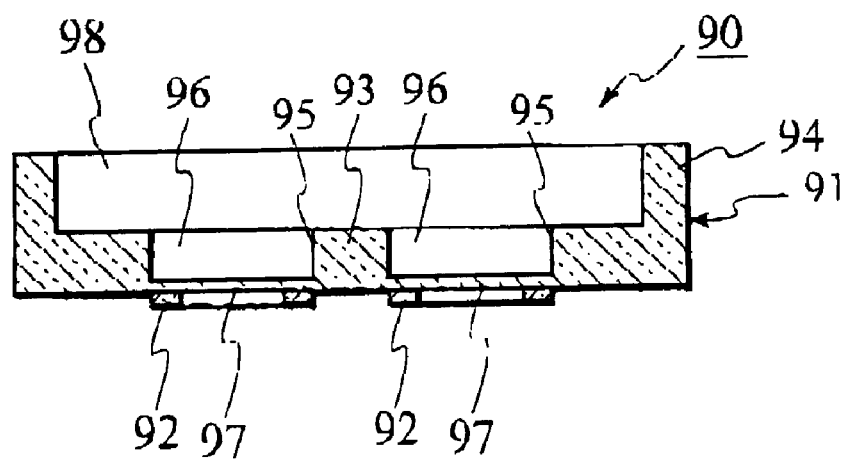
FIG. 10B is a sectional view of the reaction cell according to the tenth embodiment of the present invention, the section being shown taken along a line XB-XB of FIG. 10A.

A tenth embodiment of the present invention will be described with reference to FIGS. 10A and 10B.

A reaction cell 90 comprises a vessel-like cell main body 91 and a plurality of piezoelectric/electrostrictive oscillators 92 provided on the underside (outside surface) of the bottom portion of the cell main body 91. The cell main body 91 is constructed of a circular bottom plate portion 93, the thickness of which is great and when viewed from above the cell main body, is circular and a circumferential wall portion 94 rises from and surrounds the circumferential edge of the bottom plate portion 93, the both portions 93 and 94 being integrally formed using, for example, zirconia.

In the upper surface of the bottom plate portion 93 there are formed a pair of U-shaped recesses 95 each of which, when viewed from above, is circular in the way in which they sandwich the central part of the bottom plate portion 93. Each of these U-shaped recesses 95 forms a solution accommodation small space 96 for accommodating therein a relevant solution. And, the space which is surrounded by the circumferential wall portion 94 on the bottom portion 93 forms a solution accommodation large space 98. Incidentally, the bottom plate portion 93 is set to be relatively thick. As a result of the relatively large-depth U-shaped recesses 95 being formed in the bottom plate portion 93, the U-shaped recess 95 includes a small-thickness bottom plate 97. Incidentally, the thickness of the bottom plate 97 is set to be thin enough to permit a light to pass therethrough.

And, on the thin bottom plate 97 of each U-shaped recess 95, there are intermittently disposed and adhered along the circumferential edge of the underside of the bottom plate 97 a plurality of piezoelectric/electrostrictive oscillators 92. Incidentally, since the piezoelectric/electrostrictive oscillator 92 is not disposed at the central part of the bottom plate 97, it becomes possible, by passing a light from the central part of the bottom plate 97, to grasp the status of solution (the status of the reaction) within the U-shaped recess 95 through the change in the optical transmittance.

Incidentally, the diameter of the solution accommodation large space 98 in the reaction cell 90 can suitably be set according to the kind of the solution or the purpose of detection thereof. The other construction of the reaction cell 90 according to this embodiment is the same as that according to the sixth embodiment.

Since the reaction cell 90 according to this embodiment is constructed so that the bottom plate 77 has optical transmissivity, it is possible to detect the status of solution within the U-shaped recess 95 by measuring the optical transmittance.

The reaction cell 90 according to this embodiment may also be used in a state where the relevant solution is accommodated within only the solution accommodation small space 96 alone, or may be used in a state where the solution is accommodated within the solution accommodation large space 98. And, by driving the piezoelectric/electrostrictive oscillator 92 which causes the partial deflection oscillation of the bottom plates 97, the oscillation can be transmitted to the solution within the solution accommodation small space 96 and solution accommodation large space 98. And, because the oscillation is transmitted to the solution, the solution is agitated and a prescribed reaction of the solution is promoted.

Especially, in this embodiment, by individually driving the piezoelectric/electrostrictive oscillator 92, the flow of the solution within the solution accommodation small space 96 becomes able to be freely controlled. In addition, agitating the solution so as for it to have the form of, for example, a vortex also becomes possible whereby it is possible to enhance the agitating efficiency. Also, optimum oscillation which is in compliance with the status of the reaction can be performed in every solution accommodation small space 96.

ELEVENTH EMBODIMENT

An eleventh embodiment of the present invention will be described with reference to FIGS. 11A and 11B.

A reaction cell 100 according to this embodiment comprises a vessel-like cell main body 101 and a plurality of first piezoelectric/electrostrictive oscillators 102 provided on the underside (outside surface) of the cell main body 101, and a pair of second piezoelectric/electrostrictive oscillators 103 provided within the cell main body 101 and a plurality of third piezoelectric/electrostrictive oscillators 104.

The cell main body 101 is constructed of a first circular bottom plate portion 105, the thickness of which is great and when viewed from above, is circular and a circumferential wall portion 106 rises from and surrounds the circumferential edge of the first bottom plate portion 105, the both portions 105 and 106 being integrally formed using, for example, zirconia.

On the circumferential edge portion of the first bottom plate portion 105 there are intermittently disposed and fixed along the circumferential edge of it the third piezoelectric/electrostrictive oscillators 104. Also, in the bottom plate portion 105 there are formed a pair of first U-shaped recesses 107 at the positions that sandwich the central part of the first bottom plate portion 105. In this first U-shaped recess 107, there is formed the second piezoelectric/electrostrictive oscillator 103 in such a way that it circumferentially extends along the inner-circumferential surface of the recess 107.

Figure 11A:
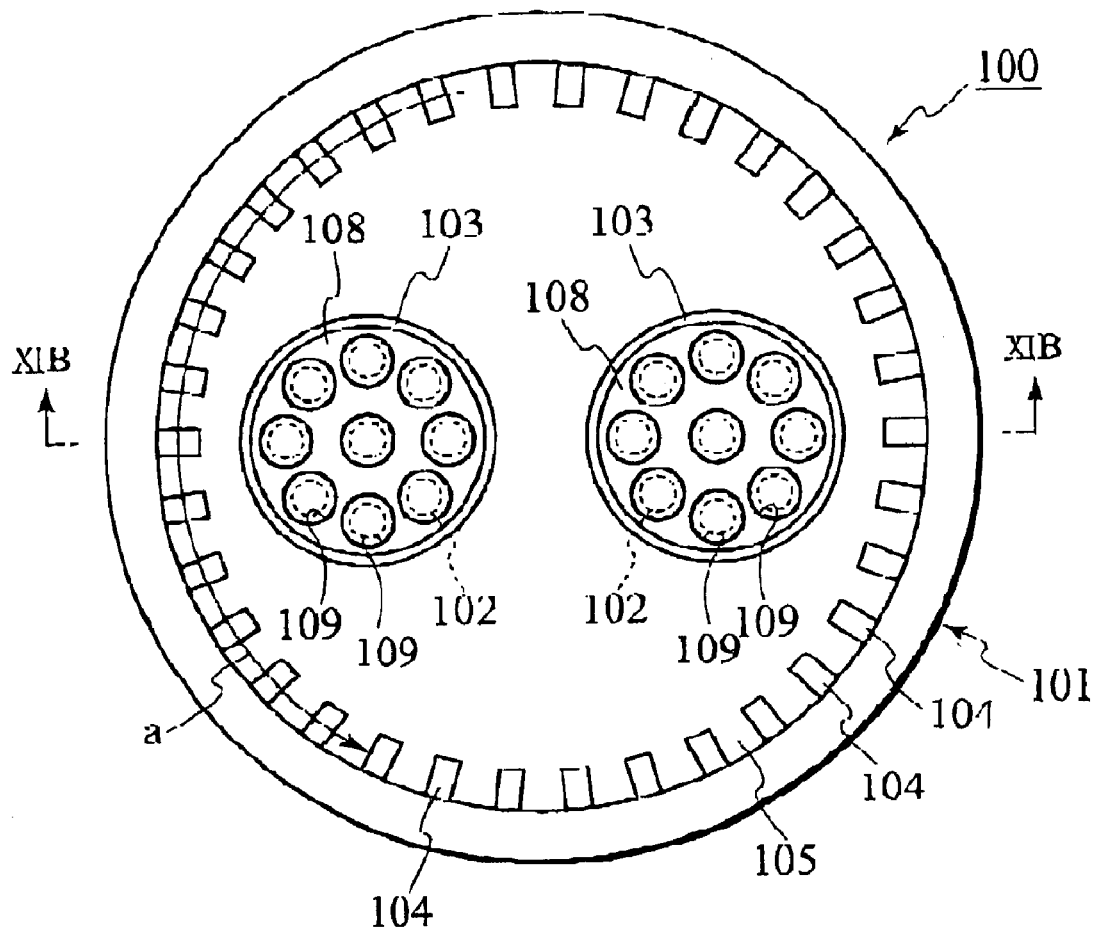
FIG. 11A is a plan view of a reaction cell according to an eleventh embodiment of the present invention.
Figure 11B:
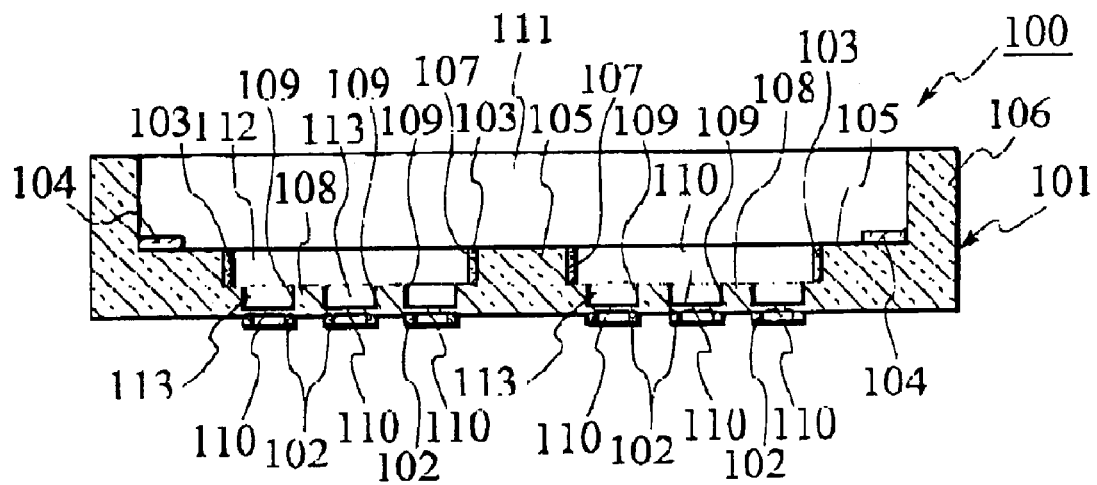
FIG. 11B is a sectional view of the reaction cell according to the eleventh embodiment of the present invention, the section being shown taken along a line XIB-XIB of FIG. 11A.

Also, on the bottom of the first U-shaped recess 107, there is formed a second bottom plate portion 108 and, in the second bottom plate portion 108, as illustrated in FIG. 11A, there are formed a plurality of second U-shaped recesses 109 at the central part and in the neighborhood thereof.

Further, in the bottom of the second U-shaped recess 109, there is formed a third bottom plate portion 110. On the underside of the third bottom plate portion 110, there is fixedly provided the above-described piezoelectric/electrostrictive oscillator 102. Incidentally, the first piezoelectric/electrostrictive oscillator 102 is in the form of an annulus and has a maximum diameter equal to the diameter of the bottom plate portion 110. Also, since the first piezoelectric/electrostrictive oscillator 102 has formed at its central part a hole, and, from this hole, the third bottom plate portion 110 is exposed.

And, the space which is surrounded by the circumferential wall portion 106 on the first bottom plate portion 108 forms a solution accommodation large space 111. Also, the space which is surrounded by the second piezoelectric/electrostrictive oscillator 103 on the second bottom plate portion 108 forms a solution accommodation middle space 112. Further, the space which is within the second U-shaped recess 109 on the third bottom plate portion 110 forms a solution accommodation small space 113.

Incidentally, the diameter of the first bottom plate portion 105 in the reaction cell 100 is preferably set to be at a value falling within a range of from several mm to several tens of cm. Also, the diameter of the second bottom plate portion 108 is preferably set to be at a value falling within a range of from several tens of μm to several mm. Further, the diameter of the third bottom plate portion 110 is preferably set to be at a value falling within a range of from several tens of μm to several mm.

In the reaction cell 100 according to this embodiment, the thickness of the third bottom plate portion 110 is set to have a small thickness so as to permit a light to pass therethrough. And, since the first piezoelectric/electrostrictive oscillator 102 does not exist at the central part of the third bottom plate portion 110, it is possible to detect the status of solution within the second U-shaped recess 109 by measuring the optical transmittance through the bottom plate portion 110.

The reaction cell 100 according to this embodiment also enables the reaction of the solution to be performed in a state where the solution is accommodated within only the solution accommodation small space 113 alone, or in a state where the solution is accommodated within the solution accommodation middle space 112, or in a state where the solution is accommodated within the solution accommodation large space 111.

And, by driving the first piezoelectric/electrostrictive oscillator 102, the oscillation which has occurred in the piezoelectric/electrostrictive oscillator 102 can be transmitted to the solution within the solution accommodation small space 113 via the third bottom plate portion 110. Also, by driving the second piezoelectric/electrostrictive oscillator 103, the oscillation can be transmitted to the solution within the solution accommodation middle space 112. Further, by driving the third piezoelectric/electrostrictive oscillator 104, the oscillation can be transmitted to the solution within the solution accommodation large middle space 111. As a result, a prescribed reaction of solution can be promoted within the reaction cell 100.

Incidentally, in the reaction cell 100, as well, according to this embodiment, the first, second and third piezoelectric/electrostrictive oscillators 102, 103, and 104 are each connected to a drive control circuit via a wiring (not illustrated) so that the number of oscillations and the oscillation length of time and so forth may suitably be controlled. Also, the plurality of third piezoelectric/electrostrictive oscillators 104 may be driven in synchronism with each other and, other than this, may also be driven in the way their driving timings are sequentially shifted in the circumferential direction illustrated by an arrow (a) in FIG. 11A. In this case, the solution within the solution accommodation large space 111 can be made to have a macro rotational flow in the circumferential direction. Also, the first to the third piezoelectric/electrostrictive oscillators 102, 103, and 104 can also be driven in a multistage way for every solution accommodation space.

Also, in the reaction cell 100, each of the first to third piezoelectric/electrostrictive oscillators 102, 103, and 104 is so arranged that it can detect the change in the viscosity that follows the change in the status of reaction of the solution within the solution accommodation small space 113, solution accommodation middle space 112, or solution accommodation large space 111 that it is located close to or it directly contacts with. Concretely, it is arranged that by detecting the electric constant following the oscillation of each piezoelectric/electrostrictive oscillator, the viscosity of the solution can be determined.

TWELFTH EMBODIMENT

A twelfth embodiment of the present invention will be described with reference to FIGS. 12A and 12B.

A reaction cell 200 according to this embodiment comprises a vessel-like cell main body 201 and a plurality of first piezoelectric/electrostrictive oscillators 202 provided on the underside (outside surface) of the cell main body 201, and a pair of second piezoelectric/electrostrictive oscillators 203 provided within the cell main body 201 and a plurality of third piezoelectric/electrostrictive oscillators 204.

The cell main body 201 is constructed of a first circular bottom plate portion 205, the thickness of which is great, and which, when viewed from above, is circular and a circumferential wall portion 206 rises from and surrounds the circumferential edge of the first bottom plate portion 205, the both portions 205 and 206 being integrally formed using, for example, plastics. Incidentally, the inside surface of the circumferential wall portion 206 is formed into a tapered surface 206A which is inclined slantwise inward and downward. On the upper portion of the tapered surface 206A of the circumferential wall portion 206 there is formed the above-described third piezoelectric/electrostrictive oscillator 204 in such a way that it circumferentially extends along the tapered surface 206A.

Also, in the bottom plate portion 205 there are formed a pair of first U-shaped recesses 207 at the positions that sandwich the central part of the first bottom plate portion 205. In this first U-shaped recess 207, there is formed the second piezoelectric/electrostrictive oscillator 203 in such a way that it circumferentially extends along the inner-circumferential surface of the recess 207.

Figure 12A:
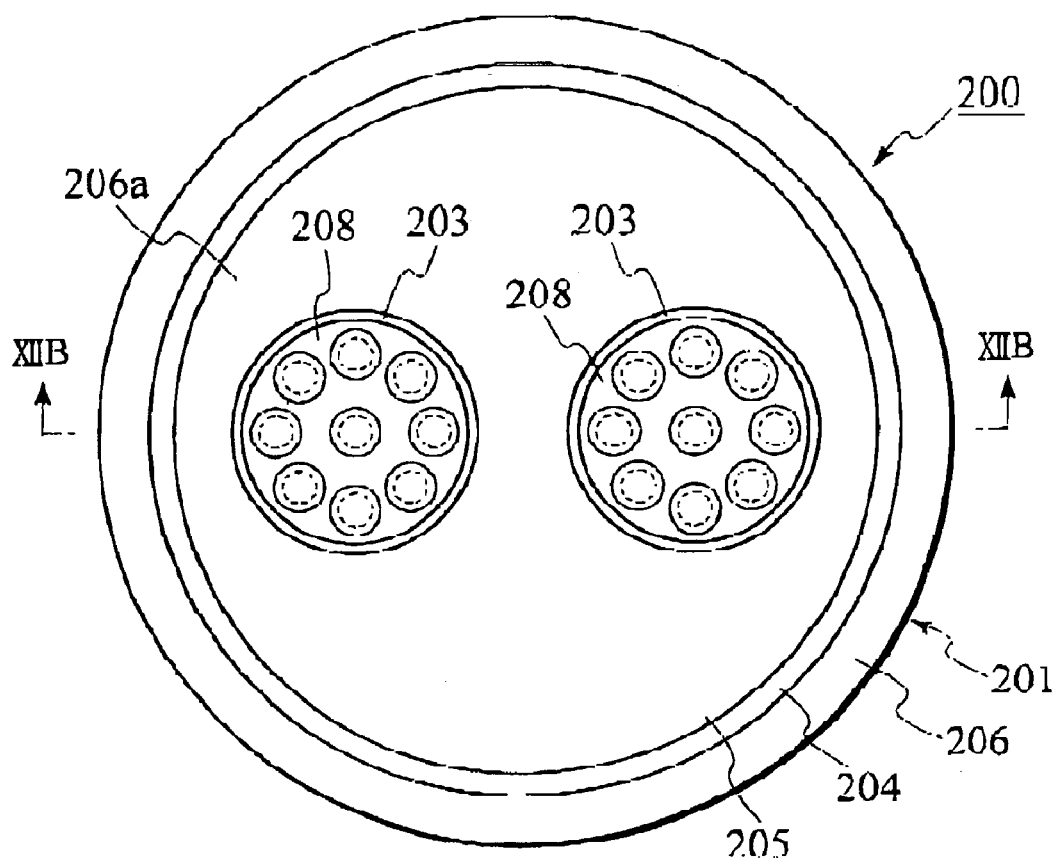
FIG. 12A is a plan view of a reaction cell according to a twelfth embodiment of the present invention.
Figure 12B:
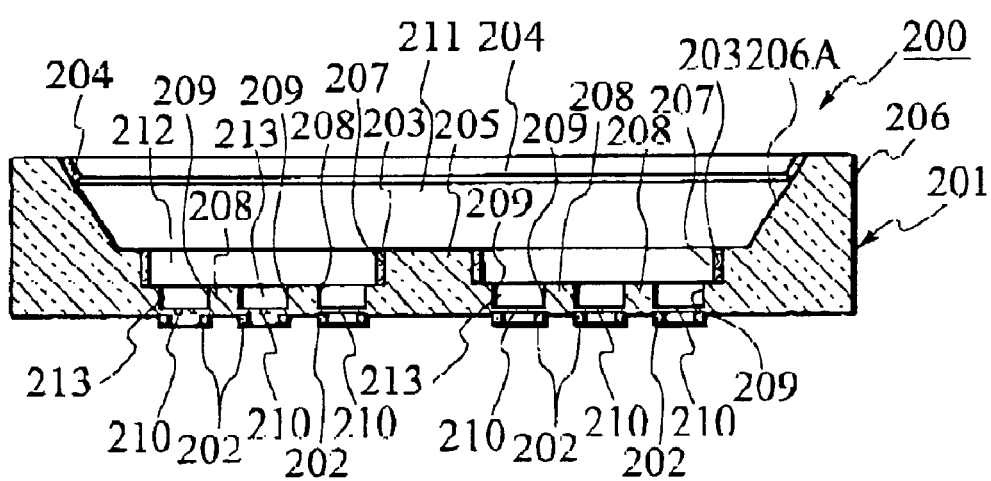
FIG. 12B is a sectional view of the reaction cell according to the twelfth embodiment of the present invention, the section being shown taken along a line XIIB-XIIB of FIG. 12A.

Further, on the bottom of the first U-shaped recess 207, there is formed a second bottom plate portion 208 and, in the second bottom plate portion 208, as illustrated in FIG. 12A, there are formed a plurality of second U-shaped recesses 209 at the central part and in the neighborhood thereof.

Further, in the bottom of the second U-shaped recess 209, there is formed a third bottom plate portion 210. On the underside of the third bottom plate portion 210, there is fixedly provided the above-described piezoelectric/electrostrictive oscillator 202. Incidentally, the first piezoelectric/electrostrictive oscillator 202 is in the form of an annulus and has a maximum diameter substantially equal to the diameter of the third bottom plate portion 210. Also, since the first piezoelectric/electrostrictive oscillator 202 has formed at its central part a hole, and, from this hole, the third bottom plate portion 210 is exposed.

The space which is surrounded by the circumferential wall portion 206 on the first bottom plate portion 205 forms a solution accommodation large space 211. Also, the space which is surrounded by the second piezoelectric/electrostrictive oscillator 203 on the second bottom plate portion 208 forms a solution accommodation middle space 212. Further, the space which is within the second U-shaped recess 209 on the third bottom plate portion 210 forms a solution accommodation small space 213.

Incidentally, the diameter of the first bottom plate portion 205 in the reaction cell 200 is preferably set to be at a value falling within a range of from several mm to several tens of cm. Also, the diameter of the second bottom plate portion 208 is preferably set to be at a value falling within a range of from several tens of μm to several mm. Further, the diameter of the third bottom plate portion 210 is preferably set to be at a value falling within a range of from several μm to several mm.

In the reaction cell 200 according to this embodiment, the thickness of the third bottom plate portion 210 is set to have a small thickness so as to permit a light to pass therethrough. And, since the first piezoelectric/electrostrictive oscillator 202 does not exist at the central part of the third bottom plate portion 210, it is possible to detect the status of solution within the second U-shaped recess 209 by measuring the optical transmittance through the third bottom plate portion 210.

The reaction cell 200 according to this embodiment also enables the reaction of the solution to be performed in a state where the solution is accommodated within only the solution accommodation small space 213 alone, or in a state where the solution is accommodated within the solution accommodation middle space 212, or in a state where the solution is accommodated within the solution accommodation large space 211.

By driving the first piezoelectric/electrostrictive oscillator 202, the oscillation which has occurred in the piezoelectric/electrostrictive oscillator 202 can be transmitted to the solution within the solution accommodation small space 213 as the deflection oscillation of the third bottom plate portion 210. Also, by driving the second piezoelectric/electrostrictive oscillator 203, the oscillation can be transmitted to the solution within the solution accommodation middle space 212. Further, by driving the third piezoelectric/electrostrictive oscillator 204, the oscillation can be transmitted to the solution within the solution accommodation large middle space 211. As a result, a prescribed reaction of solution can be promoted within the reaction cell 200.

Incidentally, in the reaction cell 200, as well, according to this embodiment, the first, second and third piezoelectric/electrostrictive oscillators 202, 203, and 204 are each connected to a drive control circuit via a wiring (not illustrated) so that the number of oscillations and the oscillation length of time and so forth may suitably be controlled.

In this embodiment, as in the case of the above-described eleventh embodiment, in the reaction cell 200, each of the first to third piezoelectric/electrostrictive oscillators 202, 203, and 204 is so arranged that it can detect the changes in the specific gravity and viscosity that follow the change in the status of reaction of the solution within the solution accommodation small space 213, solution accommodation middle space 212, or solution accommodation large space 211 that is located close to or directly contacts with one of the oscillators. Concretely, by detecting the electric constant following the oscillation of each piezoelectric/electrostrictive oscillator, the specific gravity and viscosity of the solution can be determined.

THIRTEENTH EMBODIMENT

Figure 13A:
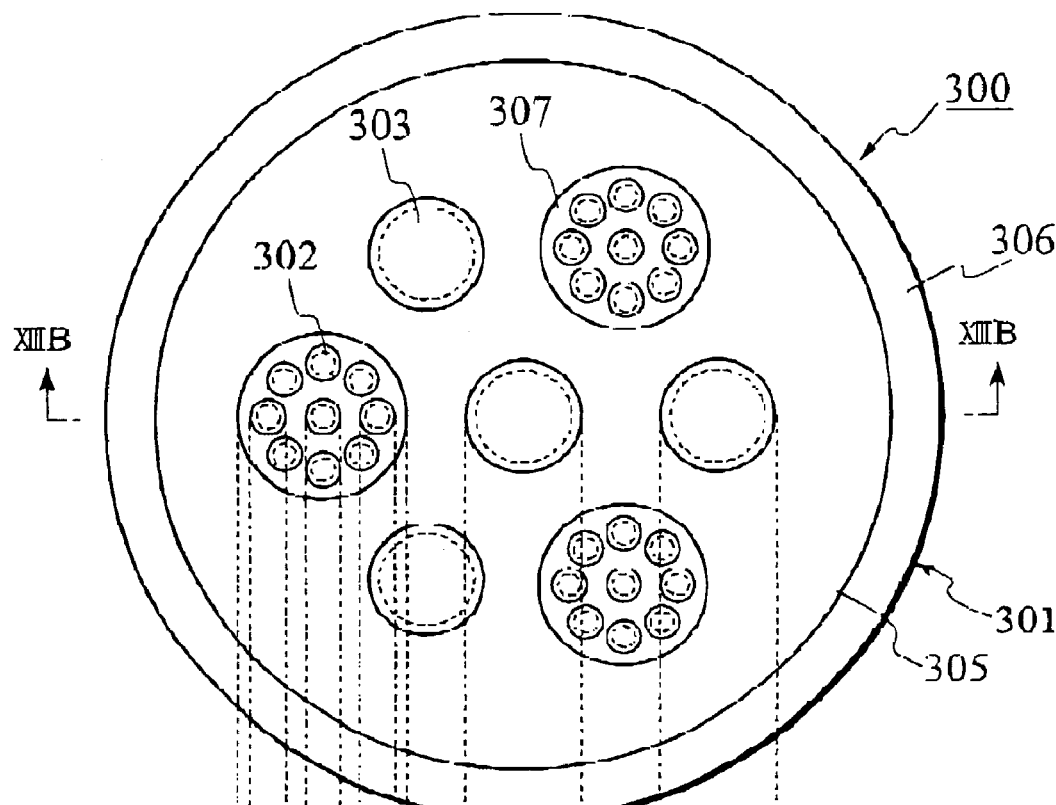
FIG. 13A is a plan view of a reaction cell according to a thirteenth embodiment of the present invention.
Figure 13B:
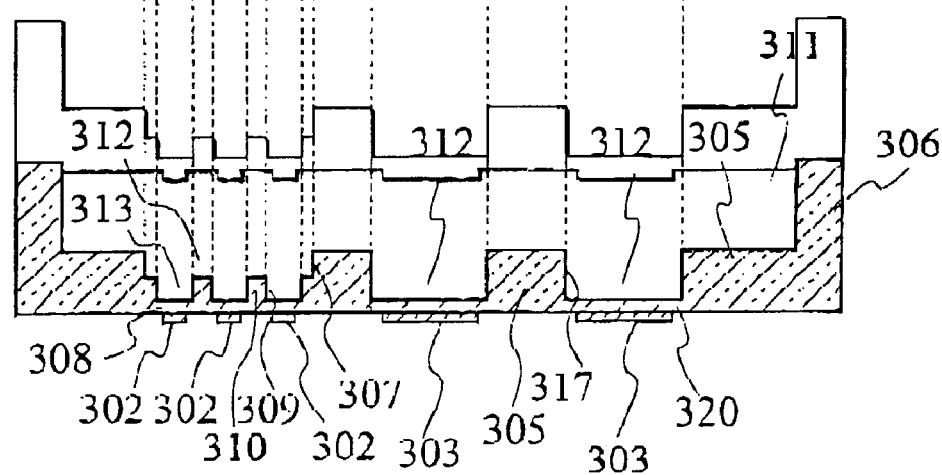
FIG. 13B is a sectional view of the reaction cell according to the thirteenth embodiment of the present invention, the section being shown taken along a line XIIIB-XIIIB of FIG. 13A.

A thirteenth embodiment of the present invention will be described with reference to FIGS. 13A and 13B.

A reaction cell 300 according to this embodiment comprises a vessel-like cell main body 301 and a plurality of first piezoelectric/electrostrictive oscillators 302 provided on the underside (outside surface) of the cell main body 301, and second piezoelectric/electrostrictive oscillators 303 provided on the underside (outside surface) of the bottom portion of the cell main body at a position other than that where the first piezoelectric/electrostrictive oscillators have been formed.

The cell main body 301 is constructed of a first circular bottom plate portion 305, the thickness of which is great and when viewed from above, is circular and a circumferential wall portion 306 rises from and surrounds the circumferential edge of the first bottom plate portion 305, the both portions 305 and 306 being integrally formed using, for example, zirconium ceramics.

In the first bottom plate portion 305, there are formed in the neighborhood of its central part a plurality of U-shaped recesses 307. In the relatively thin bottom plate 310 of each U-shaped recess 307 there are formed a plurality of second U-shaped recesses 309. On the central part of the underside of a thin bottom plate 308 of each second U-shaped recess 309 there is disposed and adhered the piezoelectric/electrostrictive oscillator 302. The piezoelectric/electrostrictive oscillator 302 is circular and has a diameter substantially equal to the diameter of the bottom plate 310. The reaction cell 300 having such structure has a solution accommodation small space 313 within the second U-shaped recess 309, a solution accommodation middle space 312 within the U-shaped recess 307, and a solution accommodation large space 311 which is surrounded by the circumferential wall portion 306 on the bottom plate 305. Further, in the first bottom plate portion 305, there are formed at the central part of it and in the neighborhood of the central part which is other than the portions where the U-shaped recesses 307 are disposed a plurality of U-shaped recesses 317. This U-shaped recess 317 is circular when viewed from above it and, on the underside of a thin bottom plate 320 at that bottom surface, there are disposed and adhered the piezoelectric/electrostrictive oscillator 303.

Incidentally, the diameter of the first bottom plate portion 305 in the reaction cell 300 is preferably set to be at a value falling within a range of from several mm to several tens of cm. Also, the diameter of the relatively thin bottom plate 310 at the second bottom plate portion is preferably set to be at a value falling within a range of from several tens of μm to several mm. Further, the diameter of the thin bottom plate 308 at the third bottom plate portion is preferably set to be at a value falling within a range of from several μm to several mm.

In the reaction cell 300 according to this embodiment, the second piezoelectric/electrostrictive oscillator 303 which has been optimally designed for movement and agitation of the solution within the solution accommodation large space 311 is formed whereby, by driving the piezoelectric/electrostrictive oscillator, it is possible to freely agitate the solution in the entire large cell including the smaller cells. Incidentally, the configuration of the U-shaped recess 317 on the bottom plate of which there is formed the second piezoelectric/electrostrictive oscillator 303 is not limited in particular but can be made into one that is suitable for moving and agitating the solution within the solution accommodation large space 311. However, to efficiently transmit the oscillation of the second piezoelectric/electrostrictive oscillator 303 to the solution, that configuration preferably is in the form of a U-shaped recess which enables using the deflection oscillation of the thin bottom plate 320.

In the reaction cell 300 according to this embodiment, it is preferable to cause the reaction of the solution to be performed in a state where the solution is accommodated within every one of the solution accommodation small space 313, solution accommodation middle space 312, and solution accommodation large space 311.

Incidentally, in the reaction cell 300 according to this embodiment, the first and second piezoelectric/electrostrictive oscillators 302 and 303 are each connected to a drive control circuit via a wiring (not illustrated) so that the number of oscillations and the oscillation length of time and so forth may suitably be controlled.

Also, in the reaction cell 300, each of the first and second piezoelectric/electrostrictive oscillators 302 and 303 is so arranged that it can detect the change in the specific gravity and viscosity that follows the change in the status of reaction of the solution within the solution accommodation small space 313, solution accommodation middle space 312, or solution accommodation large space 311, which is located close to or it directly contacts with one of the oscillators. Concretely, by detecting the electric constant following the oscillation of each piezoelectric/electrostrictive oscillator, the gravity and the viscosity of the solution can be determined. Incidentally, in the case of the reaction cell 300, since the second piezoelectric/electrostrictive oscillator 303 does not exist inside the reaction cell, when the oscillator 303 is other than when it acts on the movement and agitation of the solution, it can be exclusively used for measuring the specific gravity and viscosity. For this reason, finer monitoring becomes possible.

FOURTEENTH EMBODIMENT

A fourteenth embodiment of the present invention will be described with reference to FIGS. 14A and 14B.

The structure of a reaction cell 400 according to this embodiment is that a pair of first U-shaped recesses 107 are further added to the first bottom plate portion 105 in the reaction cell 100 according to the above-described eleventh embodiment. Other constructions are the same as those in the reaction cell 100 according to the eleventh embodiment and therefore they are denoted by the same reference numerals and their explanation will be omitted.

Figure 14A:
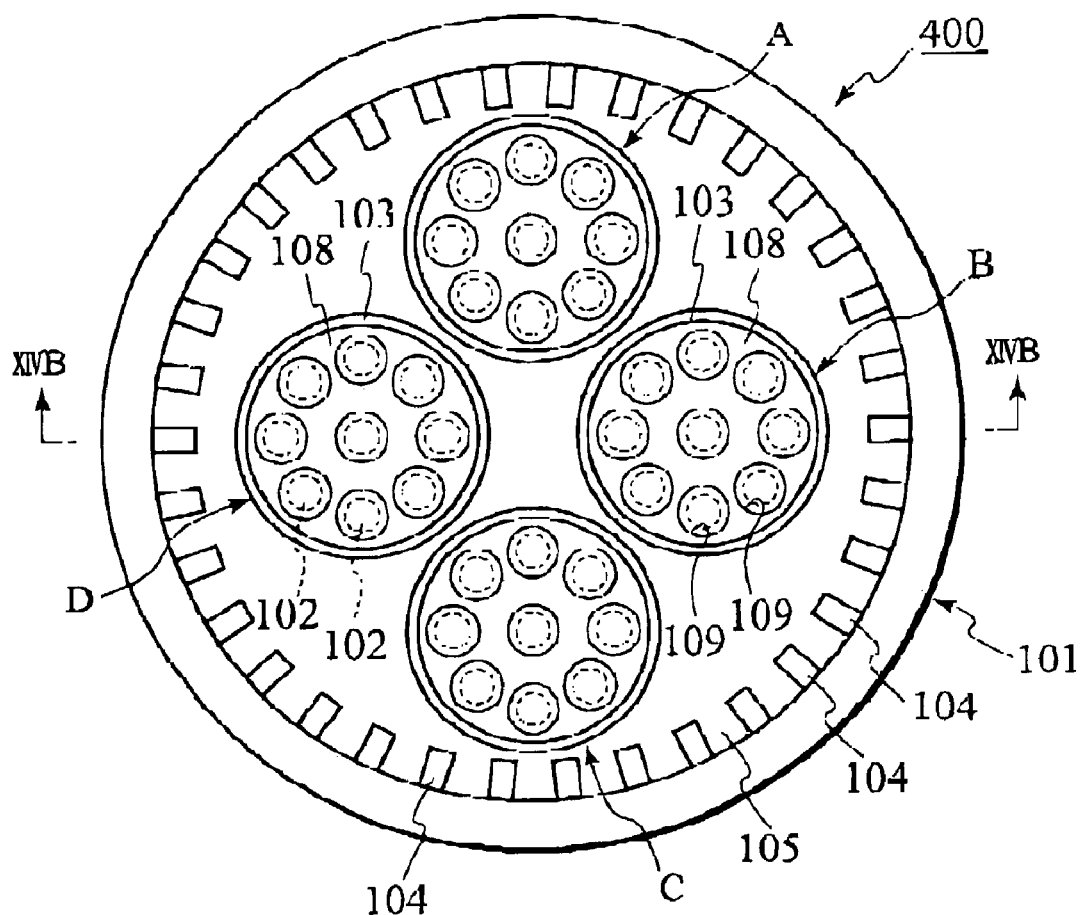
FIG. 14A is a plan view of a reaction cell according to a fourteenth embodiment of the present invention.
Figure 14B:
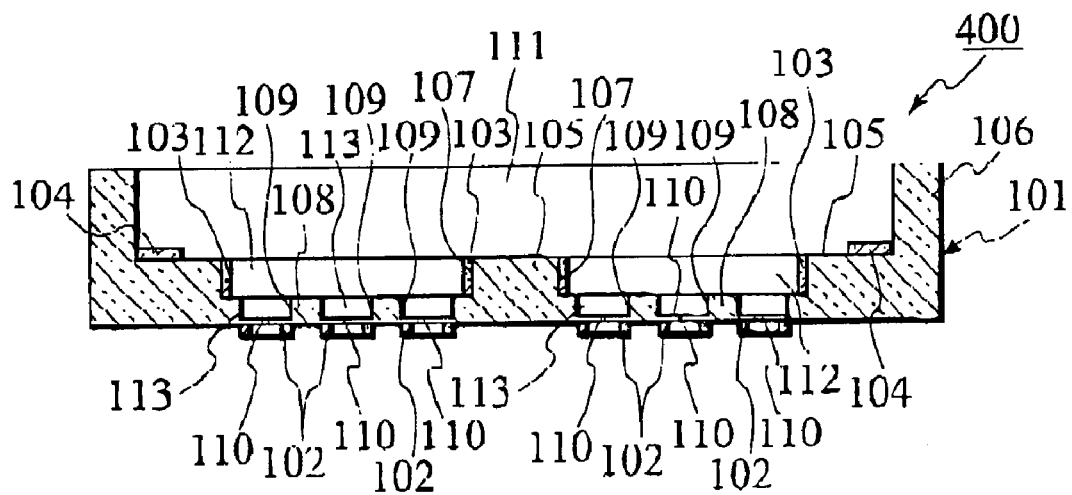
FIG. 14B is a sectional view of the reaction cell according to the fourteenth embodiment of the present invention, the section being shown taken along a line XIVB-XIVB of FIG. 14A.

Such reaction cell 400 is the one that is provided with four groups A, B, C, and D each of which includes a plurality of solution accommodation small spaces 113 such as those illustrated in FIG. 14A. The reaction cell 400 is advantageous when those groups A, B, C, and D corresponding to the solution accommodation small spaces 113 are used for immobilizing the captures having adsorption specificity such as immune bodies of different kinds. Incidentally, the method of using the reaction cell 400 will later be described.

EXAMPLES

Next, Examples that use the reaction cells according to the present invention will be described.

First of all, a reaction cell according to the present invention which is provided with a piezoelectric/electrostrictive oscillator and an ordinary cell which is not provided with a piezoelectric/electrostrictive oscillator were prepared. It is to be noted that each of the reaction cell and ordinary cell is provided with more than 15 solution accommodation spaces.

A 30% (w/v) aqueous solution of sucrose was poured into each of 15 solution accommodation spaces of each of the reaction cell and ordinary cell and was pre-incubated at a temperature of 37° C.

After each cell had been pre-incubated for 10 minutes, a fixed quantity of sucrose hydrolase was added, at intervals of 2 seconds, to the cells one lot per cell.

Next, after the enzyme was added, at various lengths of time from 1 to 60 minutes, the reaction solution was sampled from each cell and the glucose was determined (colorimetry determined with a spectrophotometer, such as an F-kit made by Berlinger/Manheim Company). The results are shown in a graph depicted in FIG. 16 along the abscissa axis of which the reaction length of time is plotted and along the ordinate axis of which the yield (the quantity of glucose produced/the quantity of sucrose added (W/W)) is plotted.

Figure 16:
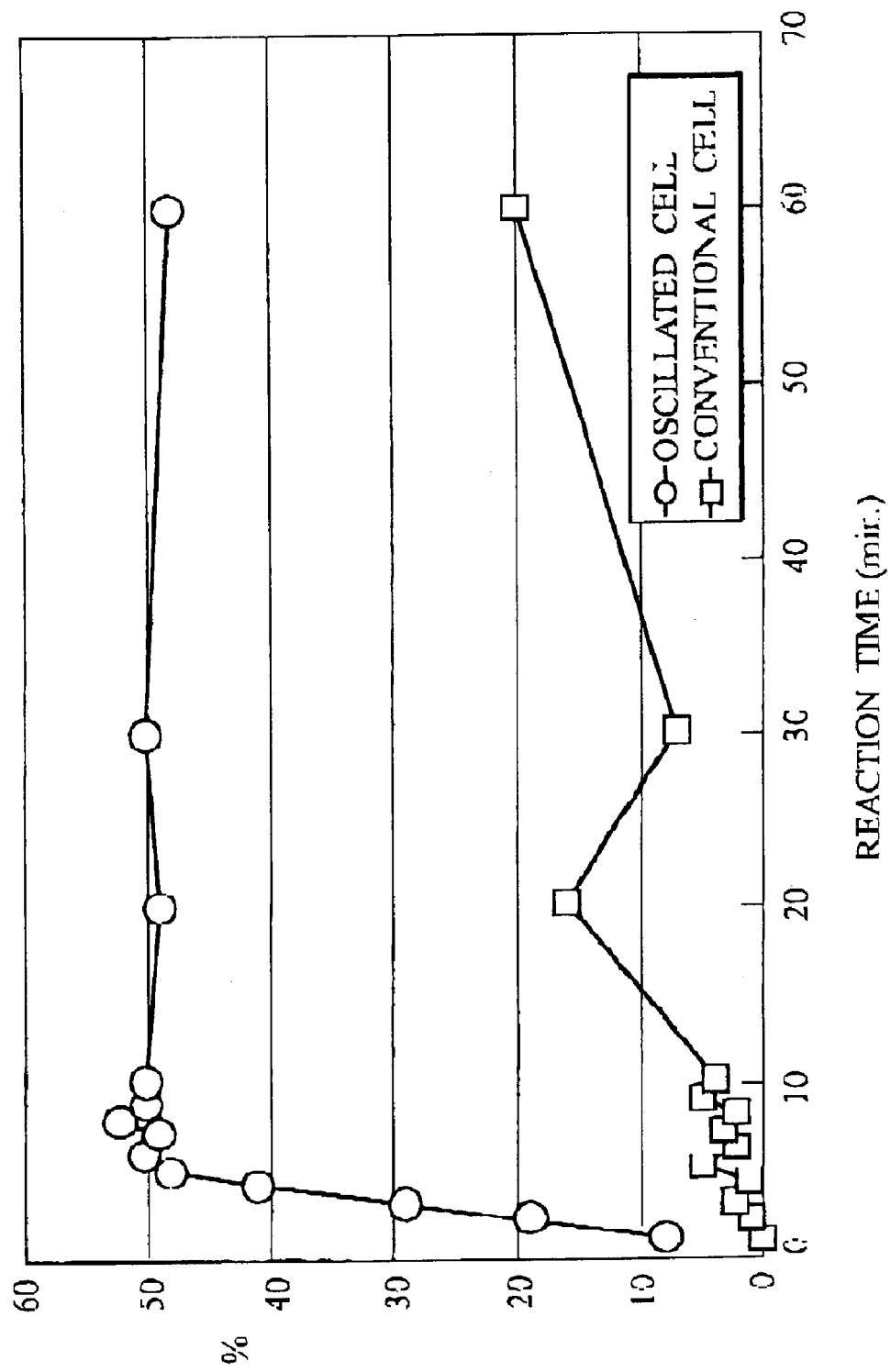
FIG. 16 is a graph illustrating the relationship between the reaction length of time and the yield of each of the reaction cell provided with a piezoelectric/electrostrictive oscillator according to the present invention and an ordinary cell according to the prior art.

As illustrated in FIG. 16, in the reaction cell (oscillation cell) according to the present invention which is provided with the piezoelectric/electrostrictive oscillator, the reaction properly proceeded up to around a theoretical value, whereas, in the ordinary cell, the speed at which the reaction proceeded was low and, in addition, data variance was also wide.

[Method of Manufacturing a Reaction Cell]

Next, various kinds of manufacturing methods according to the present invention will briefly be described.

(Method of Manufacturing Using Zirconia)

First, green sheets of zirconia were suitably laminated and were formed into a configuration as a cell main body. Thereafter, the green sheet laminate was sintered and produced into the cell main body.

Next, on the reverse surface of the bottom plate portion of the cell main body, a lower electrode, piezoelectric/electrostrictive member, and upper electrode were sequentially formed by printing and sintering techniques. By doing so, it is possible to produce a reaction cell.

(Method of Manufacturing by Cutting Working)

Alumina having optical transmissivity which was sintered in bulk was cutting worked and was worked into a configuration as a cell main body. Thereafter, a piezoelectric/electrostrictive oscillator was fabricated. In the method of fabricating a piezoelectric/electrostrictive oscillator, a lower electrode, piezoelectric/electrostrictive layer, and upper electrode were sequentially printed to a prescribed position of the cell main body, after which sintering was performed to fabricate a reaction cell.

(Method of Manufacturing by Pasting a Transparent Plate)

A cell main body is formed by laminating ceramic green sheets so that the portion where a solution is accommodated may become a through-hole. Thereafter, the laminate consisting of the ceramic green sheets is sintered. After that, a plate consisting of a transparent glass or synthetic resin is adhered to the underside of the sintered body by adhesive agent, or thermal diffusion, or thermal bond (in a case where the synthetic resin is thermoplastic resin) to thereby fabricate a cell main body. Further, a piezoelectric/electrostrictive oscillator is adhered onto a suitable position of the cell main body by using an adhesive agent to thereby fabricate a reaction cell.

(Method of Manufacturing by Using Etched Glass)

Transparent glass is etching worked and a U-shaped recess is thereby formed. After that, a piezoelectric/electrostrictive oscillator is adhered onto the resulting structure by using an adhesive agent to thereby fabricate a reaction cell.

(Method of Manufacturing by using a transparent synthetic Resin)

Transparent synthetic resin material is poured into a die to thereby form a cell main body, and a piezoelectric/electrostrictive oscillator is adhered onto a suitable position by using an adhesive agent to thereby form a reaction cell.

Although various kinds of the manufacturing methods for fabricating a reaction cell have been described as above, in a case where, for example, a capture having adsorption specificity needs to be adhered to within the reaction cell, as one method the capture may be immobilized to the reaction cell which has been manufactured with the above-described method. However, as an alternative to that, a transparent glass or transparent synthetic resin having immobilized thereto beforehand the capture may be adhered to a wall portion of the cell main body.

Incidentally, when fabricating a piezoelectric/electrostrictive oscillator, the process step wherein pastes containing therein respective raw materials of a lower electrode, piezoelectric/electrostrictive element layer, and upper electrode are printed onto the cell main body by screen printing is repeatedly executed for every one of the lower electrode, piezoelectric/electrostrictive element layer, and upper electrode, to thereby form a laminate. Then, the laminate needs only to be sintered. Or, a respective one of the pastes may be sintered for every printing, or both techniques may be combined together. Here, as the method of supplying the pastes containing therein the raw materials onto the ceramics, in a case where supplying them to the underside of the bottom plate portion, they can be supplied by screen printing. However, in a case where supplying them to the circumferential wall portion, a through-hole printing technique may be used, or they may be supplied by dipping into the solution containing therein the respective raw materials the cell main body having masked its portions where the piezoelectric/electrostrictive oscillator is not formed. Also, especially the upper electrode is not limited to being formed by printing, dipping, and sintering but may be formed by using a thin film forming technique such as a sputtering technique, a deposition technique, etc.

[Method of Using a Reaction Cell]

The method of using the reaction cell 400 according to the above-described thirteenth embodiment will be described next with reference to FIG. 15.

(First Method of Using)

Figure 15:
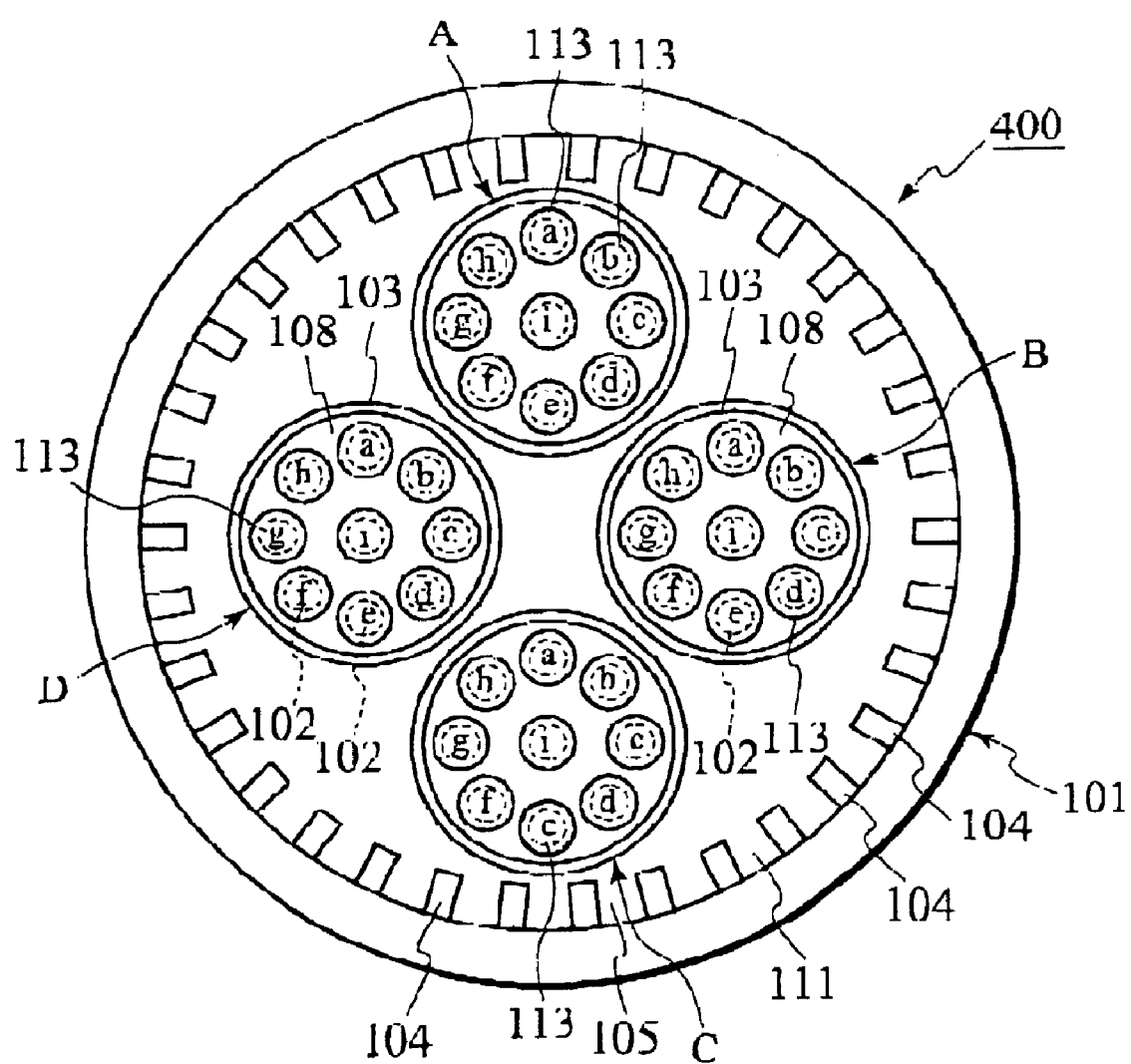
FIG. 15 is a plan view illustrating an example of a method of using a reaction cell according to the present invention.

FIG. 15 shows that groups A, B, C, and D each include 9 solution accommodation small spaces 113 and reference letters a, b, c, d, e, f, g, h, and i sequentially represent 8 small spaces and 1 center space, respectively, clockwise as shown in FIG. 15. Into each of the spaces a to h, there is poured a different diluted stage of enzyme solution, the activity of which is unknown. Here, the space i is left blank. After that, the first piezoelectric/electrostrictive oscillator 102, which is provided on the underside of the space having the solution accommodated therein, is driven for a prescribed length of time to thereby transmit a prescribed strength of oscillation to the solution within each space. After the passage of a prescribed reaction length of time, the status of the solution is detected by performing a colorimetry analysis of the solution in each space or by measuring the viscosity of the solution. Incidentally, colorimetry can be performed, for example, by radiating a light from a position above the reaction cell 400 toward a position below it and by measuring the optical transmittance of a light, passing through the third bottom plate portion 110, on the side of the underside of the reaction cell 400. Also, the measurement of the viscosity may be performed simply by detecting the change in the electric constant following the oscillation of the first piezoelectric/electrostrictive oscillator 102 and by determining the viscosity of the solution. By detecting the status of the solution in that way, it is possible to calculate the activity (U) of the enzyme.

(Second Method of Using)

Into each of the spaces a to h illustrated in FIG. 15, there is poured a different diluted stage of enzyme solution, the activity of which is unknown. Here, the space i is made blank. Next, by driving the first piezoelectric/electrostrictive oscillator 102 and by, after the passage of a prescribed length of time, (even when it is unclear what kind of reaction has been proceeding in that state) putting a mixed solution of enzyme substrate that is predicted into the solution accommodation middle space 112, the resulting solution is caused to react. At this time, the second piezoelectric/electrostrictive oscillator 103 which surrounds solution accommodation middle space 112 is driven and the solution is agitated, thereby the reaction is promoted.

By performing colorimetry or measuring the viscosity of the solution in the same way as in the above-described method, it is determined which substrate has reacted. By doing so, the function of the enzyme and the specificity of the substrate can be determined.

(Third Method of Using)

Into the groups A, B, C, and D each having the solution accommodation small spaces illustrated in FIG. 15, there are immobilized, respectively, the captures having adsorption specificity such as for different kinds of antibodies sampled from respective organs (e.g. liver, spleen, blood, and large intestine) of a living organism. Into the solution accommodation middle spaces 112 of the respective groups, there are added the samples taken away from the respective organs. At this time, the first and second piezoelectric/electrostrictive oscillators 102, 103 are driven. By this driving, the solution within the respective solution accommodation middle spaces 112 is agitated, thereby a biochemical reaction is promoted.

After the passage of a prescribed reaction length of time, the degree of progress of the reaction in each of the groups A, B, C, and D is determined by performing pattern recognition, and, by this, it is possible to determine whether the relevant organ has an abnormality. That pattern recognition can be performed, because the third bottom plate portion 110 has optical transmissivity, from the side of the underside of the reaction cell 400.

As is apparent from the foregoing explanation, in the present invention, by setting the length of time during which the piezoelectric/electrostrictive oscillator oscillates, the intervals at which the oscillation is made, etc., it is possible to control the degree of the progress of the reaction of the solution and the reaction length of time and so forth. For this reason, it is possible to perform sufficient, uniform agitation with no contamination occurring between the cells and within a very small space. Since the configuration of the piezoelectric/electrostrictive oscillator can be freely designed, optical sensing is possible, i.e. it is possible to optically grasp the status of the solution.

According to the present invention, when the chemical reaction of the solution proceeds and for example the specific gravity, viscosity, etc. of the solution has varied, it is possible to detect the change in the electric constant following the oscillation of the piezoelectric/electrostrictive oscillator and, thereby, to detect the status of the reaction, and, further, the degree of progress of the reaction and the status of the reaction. Therefore, it is possible to perform optimum oscillation while sensing the status of the specific gravity, viscosity, etc.

Further, according to the present invention, it is possible to perform the control of the agitation, the control of the reaction, the detection of the status, etc. for every cell by controlling the operation of the piezoelectric/electrostrictive oscillator provided for the relevant cell. Also, it is possible for the piezoelectric/electrostrictive oscillator to transmit its oscillation directly to the solution and it is possible to independently control the oscillation for every cell.

Also, by driving the piezoelectric/electrostrictive oscillator provided for the cell including a plurality of cells, it is possible to evenly agitate the solution in these cells as a whole. In addition, regarding the respective individual cells that are included, they can be agitation controlled by using the relevant piezoelectric/electrostrictive oscillators.

Further, it is possible to detect the change in the electric constant following the oscillation of the piezoelectric/electrostrictive oscillator, and, thereby, to detect the specific gravity, viscosity, etc. of the solution, and, thereby, to detect the status of the reaction of the solution.

The contents of Japanese Patent Application No. 2002-56041 (filed on Mar. 1, 2002) are incorporated herein by reference in its entirety.

Although the invention has been described above by reference to certain embodiments of the invention, the invention is not limited to the embodiments described above. Modifications and variations of the embodiments described above will occur to those skilled in the art, in light of the above teachings.

For instance, although in the above-described eleventh to fourteenth embodiments the spaces which are formed in the reaction cell have been provided in three stages of the solution accommodation large space, solution accommodation middle space, and solution accommodation small space, the spaces may also be constructed in a larger number of stages, i.e. in the way the reaction cell has a solution accommodation space wherein smaller U-shaped recesses are formed in the bottoms of the solution accommodation small spaces. Namely, within a large solution accommodation space, solution accommodation spaces the sizes of which are sequentially reduced may be formed stepwise so that they may form a piece of nesting.

Also, in the reaction cell of the present invention, the number of the solution accommodation spaces formed in the interior thereof can suitably be changed according to the solution used and the purpose of the analysis. For example, they may be disposed in the form of a matrix.

What is claimed is:

1. A reaction cell comprising:
a cell having a main body including a circumferential wall portion and a bottom portion forming a space to accommodate a solution, said main body comprising at least one of ceramic and glass; and
a piezoelectric/electrostrictive oscillator formed integrally with at least one of a surface of the circumferential wall portion and at least a part of the bottom portion so as to agitate the solution,
wherein the bottom portion of the cell further comprises one or more first recess portions, and a bottom portion of the first recess portions comprises one or more second recess portions which accommodate the solution.

2. The reaction cell of claim 1, wherein the piezoelectric/electrostrictive oscillator is disposed proximate to one or more of the first recess portions.

3. The reaction cell of claim 1, wherein the piezoelectric/electrostrictive oscillator is disposed proximate to the bottom portion of at least one of the second recess portions.

4. A method of using a reaction cell, comprising:
accommodating a solution in a first reaction cell in which one or more second reaction cells are provided at a bottom surface of said first reaction cell and a plurality of piezoelectric/electrostrictive oscillators are disposed along at least one of a circumferential wall surface of said first reaction cell and said bottom surface of said first reaction cell at positions other than where said one or more second reaction cells are located; and
oscillating said plurality of piezoelectric/electrostrictive oscillators sequentially in a circumferential direction of said first reaction cell.

5. A method of using a reaction cell, comprising:
accommodating a solution in a first reaction cell in which one or more second reaction cells are provided at a bottom surface of said first reaction cell and a plurality of piezoelectric/electrostrictive oscillators are fixed directly to at least one of a circumferential wall surface of said first reaction cell and a bottom surface of said first reaction cell at positions other than where said one or more second reaction cells are located; and
oscillating said plurality of piezoelectric/electrostrictive oscillators with an amplitude and a timing that are independently controlled,
wherein at least a portion of said plurality of piezoelectric/electrostrictive oscillators have no optical transmissivity.

6. The method of using the reaction cell of claim 4, further comprising detecting electric constant changes of the piezoelectric/electrostrictive oscillators accompanying oscillation thereof so as to measure viscosity of the solution to judge a reaction condition thereof.

* * * * *

UNITED STATES PATENT AND TRADEMARK OFFICE
CERTIFICATE OF CORRECTION

| | | |
|---|---|---|
| PATENT NO. | : 7,341,697 B2 | Page 1 of 1 |
| APPLICATION NO. | : 10/377579 | |
| DATED | : March 11, 2008 | |
| INVENTOR(S) | : Yukihisa Takeuchi, Yasuko Yoshida and Toshikazu Hirota | |

It is certified that error appears in the above-identified patent and that said Letters Patent is hereby corrected as shown below:

<u>Title Page</u>

Item (56), References Cited, U.S. Patent Documents

*Please add:*

5,462,604*    10/1995    Shibano et al.

Signed and Sealed this

Seventh Day of October, 2008

JON W. DUDAS
*Director of the United States Patent and Trademark Office*